United States Patent
Zöllner et al.

(10) Patent No.: US 10,868,254 B2
(45) Date of Patent: Dec. 15, 2020

(54) PHOSPHORESCENT OLED AND HOLE TRANSPORTING MATERIALS FOR PHOSPHORESCENT OLEDS

(71) Applicant: Novaled GmbH, Dresden (DE)

(72) Inventors: Mike Zöllner, Dresden (DE); Jens Wutke, Dresden (DE); Martin Burkhardt, Dresden (DE)

(73) Assignee: Novaled GmbH, Dresden (DE)

( * ) Notice: Subject to any disclaimer, the term of this patent is extended or adjusted under 35 U.S.C. 154(b) by 0 days.

(21) Appl. No.: 16/290,164

(22) Filed: Mar. 1, 2019

(65) Prior Publication Data

US 2019/0198767 A1 Jun. 27, 2019

Related U.S. Application Data

(62) Division of application No. 14/436,386, filed as application No. PCT/EP2013/071742 on Oct. 17, 2013, now Pat. No. 10,243,146.

(30) Foreign Application Priority Data

Oct. 17, 2012 (EP) .................................... 12188828

(51) Int. Cl.
*C07C 211/51* (2006.01)
*C07C 211/54* (2006.01)
(Continued)

(52) U.S. Cl.
CPC ........ *H01L 51/0059* (2013.01); *C07C 211/54* (2013.01); *C07C 211/56* (2013.01);
(Continued)

(58) Field of Classification Search
CPC ..................................................... C07C 211/54
See application file for complete search history.

(56) References Cited

U.S. PATENT DOCUMENTS 5,514,508 A * 5/1996 Fukami ................ G03G 5/0605
430/58.35
8,653,537 B2 2/2014 He et al.
(Continued)

FOREIGN PATENT DOCUMENTS

EP 687 668 A2 * 5/1995 ........... C07C 211/54
JP 3-94259 A * 4/1991 ............... G03G 5/06
(Continued)

OTHER PUBLICATIONS

Japanese Office Action for JP Application No. 2015-537255 dated Sep. 7, 2017 (8 pages) (English translation).
(Continued)

*Primary Examiner* — Rip A Lee
(74) *Attorney, Agent, or Firm* — Eversheds Sutherland (US) LLP

(57) ABSTRACT

The present invention relates to phosphorescent organic light-emitting diodes (OLEDs) including a hole-transporting or a hole-transporting and an electron-blocking layer including an N,N,N',N'-tetraaryl-phenylene-3,5-diamine or an N,N,N',N'-tetraaryl-1,1'-biphenyl-3,3'-diamine matrix compound and to new N,N,N',N'-tetraarylsubstituted m-arylene diamine compounds useful as hole-transporting and electron-blocking layer matrices in phosphorescent OLEDs.

10 Claims, 12 Drawing Sheets

(51) Int. Cl.
*H01L 51/00* (2006.01)
*C07D 471/04* (2006.01)
*C07D 209/82* (2006.01)
*C07C 211/56* (2006.01)
*C07C 217/94* (2006.01)
*C07D 213/38* (2006.01)
*H01L 51/50* (2006.01)
*H01L 51/52* (2006.01)

(52) U.S. Cl.
CPC .......... *C07C 217/94* (2013.01); *C07D 209/82* (2013.01); *C07D 213/38* (2013.01); *C07D 471/04* (2013.01); *H01L 51/0061* (2013.01); *C07C 211/51* (2013.01); *H01L 51/0067* (2013.01); *H01L 51/0085* (2013.01); *H01L 51/5016* (2013.01); *H01L 51/5024* (2013.01); *H01L 51/5056* (2013.01); *H01L 51/5096* (2013.01); *H01L 51/5206* (2013.01); *H01L 51/5221* (2013.01); *H01L 2251/308* (2013.01)

(56) References Cited

U.S. PATENT DOCUMENTS

| | | | |
|---|---|---|---|
| 8,980,441 B2* | 3/2015 | Kitamura | H01L 51/0061 428/690 |
| 2004/0214040 A1 | 10/2004 | Lee et al. | |
| 2009/0091249 A1 | 4/2009 | Yamaguchi et al. | |
| 2010/0155712 A1* | 6/2010 | Kitamura | H01L 51/0059 257/40 |

FOREIGN PATENT DOCUMENTS

| | | | | | |
|---|---|---|---|---|---|
| JP | 3-94260 | A * | 4/1991 | ............... | G03G 5/06 |
| JP | 4-225363 | A * | 8/1992 | ............... | G03G 5/06 |
| JP | 5-105647 | A * | 4/1993 | ............ | C07C 211/54 |
| JP | 6-110228 | A * | 4/1994 | ............... | G03G 5/06 |
| JP | 7-324058 | A * | 12/1995 | ............ | C07C 211/54 |
| JP | 07-324058 | | 12/1995 | | |
| JP | 08-278642 | A | 10/1996 | | |
| JP | 2001-281893 | A | 10/2001 | | |
| JP | 2002-241352 | * | 8/2002 | ............ | C07C 211/54 |
| JP | 2002-241352 | A | 8/2002 | | |
| JP | 2005-071983 | A | 3/2005 | | |
| JP | 2005-145010 | A | 6/2005 | | |
| JP | 2006-106677 | A | 4/2006 | | |
| JP | 2006-156635 | A | 6/2006 | | |
| JP | 2011-146743 | A * | 7/2011 | ............. | H01L 51/50 |
| JP | 2011-193004 | | * 9/2011 | ............. | H01L 51/50 |
| JP | 2011-193004 | A * | 9/2011 | ............. | H01L 51/50 |
| JP | 2012-161529 | A | 8/2012 | | |
| WO | WO 2010/004887 | A1 * | 1/2010 | ............. | C09K 11/06 |
| WO | WO 2011/155742 | A2 * | 12/2011 | ............. | C09K 11/06 |
| WO | 2012/161554 | A9 | 11/2012 | | |

OTHER PUBLICATIONS

JP 5-105647 A (Apr. 27, 1993) Ueda, Hideaki—machine translation.
JP 2011-193004 A (Sep. 29, 2011) Tanaka, Tatsuo—machine translation.
JP 2002-241352 A (Aug. 28, 2002), Ueda et al.—machine translation.
PCT International Search Report for PCT Application No. PCT/EP2013/071742 dated Nov. 6, 2013 (2 pages).
European Search Report for EP Application No. 12 18 8828 dated Mar. 21, 2013 (5 pages).
Chinese Office Action for CN Application No. 201380054463.X dated May 4, 2016 (10 pages) (English translation).
Taiwanese Office Action for TW Application No. 102137587 dated Mar. 2, 2017 (4 pages) (English translation).
Japanese Office Action for KR Application No. 10-2015-7012196 dated Mar. 4, 2020 (13 pages) (English translation).

* cited by examiner a)

b)

PHOSPHORESCENT OLED AND HOLE TRANSPORTING MATERIALS FOR PHOSPHORESCENT OLEDS

CROSS REFERENCE TO RELATED APPLICATIONS

This application is a divisional application of U.S. patent application Ser. No. 14/436,386, filed Apr. 16, 2015, now U.S. Pat. No. 10,243,146, which is a U.S. national stage application of International Application No. PCT/EP2013/071742, filed Oct. 17, 2013, which claims priority to European Application No. 12188828.3, filed on Oct. 17, 2012. The contents of these applications are hereby incorporated by reference.

The present invention relates to phosphorescent organic light-emitting devices, and to compounds which may be used in such devices, especially in hole transporting and/or electron blocking layers thereof.

In OLEDs, the electroluminescence (EL) characteristic of certain organic materials is used. In EL devices, an application of a voltage creates suitable charge carriers which form, if re-combined, activated conditions, which return into the basic condition by emission of light. For improving the efficiency, the organic light-emitting diodes very often have, amongst the emission layer, also charge transporting layers which are responsible for transport of negative and positive charge carriers into the emission layer. These charge transporting layers are grouped, depending on the charge carrier transported, into hole conductors and electron conductors. A quite similar set of layers is known for photovoltaic devices, such as organic solar cells. Organic semiconducting devices having several layers can be produced by known methods, for example evaporation under vacuum or deposition from solution.

In other words, in case of organic light-emitting diodes, light is produced and emitted by the injection of charge carriers, electrons from one side, holes from the other, from the contacts into adjacent organic layers as a result of an externally applied voltage, subsequent formation of excitons (electron-hole pairs) in an active zone, and radiant recombination of these excitons. The most usual OLED structure with the positive electrode (anode) adjacent to the substrate is schematically depicted on FIG. 1, wherein the numbers 1-9 stand for the following layers:

1. Substrate
2. Base electrode, hole-injecting (positive pole), usually transparent
3. Hole-injecting layer
4. Hole-transporting layer (HTL)
5. Light-emitting layer (EL)
6. Electron-transporting layer (ETL)
7. Electron-injecting layer
8. Cover electrode (usually a metal with low work function, electron-injecting (negative pole))
9. Encapsulation, to shut out ambient influence.

While the foregoing represents the most typical case, often several layers may be omitted, or else one layer may be combined for several properties.

An important property of organic semiconducting materials is their conductivity. The conductivity of a thin layer sample can be measured by, for example, the so-called two-point method. At this, a voltage is applied to the thin layer and the current flowing through the layer is measured. The measured resistance, respectively conductivity, results by considering the geometry of the contacts and the thickness of the layer of the sample.

In an OLED, the operational voltage (or, more exactly, the overall electrical resistance) is given not only by resistances and thicknesses of particular layers, but also by energetic barriers for charge carrier injection from a particular layer to the adjacent one. The power efficiency of the device (conversion of the electrical power in the light flux at the given wavelength or in the given colour range) depends on Joule losses given by the overall resistance and on the efficiency of conversion of charge carriers in photons, which depends on the charge carrier (electron-hole) balance and on the quantum efficiency of radiating recombination of the formed electron-hole pairs (excitons) in the device.

There is steady effort to develop materials and OLED designs which allow minimizing Joule losses, ensure the charge carrier balance and maximize the quantum efficiency. In minimizing Joule losses, significant improvement brought the design of special charge injecting layers and the introduction of electrically doped charge transporting layers. Specific charge injecting and blocking layers can also improve the charge carrier balance. Most important improvement in quantum efficiency brought an introduction of phosphorescent emitters, which allow exploiting not only singlet excitons, but also the triplet exciton states, which under normal circumstances statistically prevail in the exciton population.

In the prior art, a number of materials used for preparing hole transport layer and/or electron/exciton blocking layer is known.

However, despite impressive results in OLED performance achieved thank to previous material and design development, the OLED efficiency is still significantly below its theoretical limits and many other OLED-performance parameters like luminosity and lifetime can be also further improved.

It is therefore an object of the present invention to provide improved phosphorescent OLEDs having lower operating voltage and/or higher efficiency than devices using hole transporting and electron blocking matrices according to the state of the art. Another object of the invention is providing new compounds which can be used as matrix materials for hole-transporting layers and/or electron/exciton blocking layers which overcome the drawbacks of the prior art and can especially be used in phosphorescent OLEDs.

This object is achieved by an OLED comprising between anode and cathode at least one emitting layer comprising a phosphorescent emitter and at least one hole transporting layer comprising a compound represented by general formula (I)

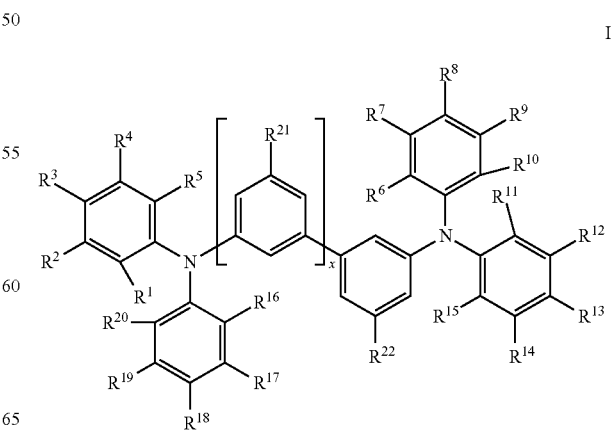

I wherein $R^1$-$R^{20}$ can be independently selected from hydrogen, C1-C20 alkyl or C3-C20 cycloalkyl, C1-C20 alkoxy or C3-C20 cycloalkyloxy, C7-C20 arylalkyl, C6-C20 aryl and C2-C20 heteroaryl, i) at least one of $R^1$-$R^5$ and at least one of $R^{11}$-$R^{15}$ is C6-C20 aryl or C2-C20 heteroaryl or ii) $R^1$ with $R^2$ as well as $R^{11}$ with $R^{12}$ form an aromatic ring or iii) $R^2$ with $R^3$ as well as $R^{12}$ with $R^{13}$ form an aromatic ring;

at least two of $R^6$-$R^{10}$ and at least two of $R^{16}$-$R^{20}$ are methyl, or at least one of $R^6$-$R^{10}$ and at least one of $R^{16}$-$R^{20}$ is selected from C2-C20 alkyl, C3-C20 cycloalkyl, C1-C20 alkoxy, C3-C20 cycloalkyloxy, C7-C20 arylalkyl, C6-C20 aryl and C2-C20 heteroaryl and x is an integer chosen from 0 and 1, wherein for x=0, $R^{22}$ has the same meaning as $R^1$-$R^{20}$ whereas for x=1, $R^{21}$ and $R^{22}$ are independently selected from hydrogen, C1-C10 alkyl, C3-C10 cycloalkyl, C1-C10 alkoxy and C3-C10 cycloalkyloxy. The alkyl or alkoxy substituent can be saturated or unsaturated, straight or branched. The cycloalkyl or cycloalkoxy substituent may be saturated or unsaturated, monocyclic or polycyclic. The overall C atom count in a substituent includes possible alkyl substitution, branching and/or occurrence of cyclic structures within the substituent. It is advantageous, if the heteroaryl substituent is attached through a carbocyclic ring or through a five-membered heterocyclic ring containing up to three heteroatoms independently chosen from O, N and S. Preferably, the overall C atom count in the compound (I) does not exceed 150. More preferably, the overall C atom count in any group of substituents selected from $R^1$-$R^5$, $R^6$-$R^1$, $R^{11}$-$R^{15}$, $R^{16}$-$R^{20}$, that means of all the substituents bound to one of phenyl rings bound in the structure (I) to nitrogen atoms, does not exceed 20. Most preferably, the overall C atom count in any group of substituents selected from $R^1$-$R^5$, $R^6$-$R^1$, $R^{11}$-$R^{15}$, $R^{16}$-$R^{20}$ does not exceed 12.

In a preferred embodiment, at least one of $R^1$-$R^5$ and at least one of $R^{11}$-$R^{15}$ is C6-C20 aryl or C2-C20 heteroaryl, whereas other $R^1$-$R^5$ and $R^{11}$-$R^{15}$ are hydrogen. In a more preferred embodiment, at least one of $R^1$-$R^5$ and at least one of $R^{11}$-$R^{15}$ is phenyl, whereas other $R^1$-$R^5$ and $R^{11}$-$R^{15}$ are hydrogen. In another preferred embodiment, at least two of $R^6$-$R^{10}$ and at least two of $R^{16}$-$R^{20}$ are methyl, or at least one of $R^6$-$R^{10}$ and at least one of $R^{16}$-$R^{20}$ is selected from C2-C20 alkyl, C3-C20 cycloalkyl, C1-C20 alkoxy, C3-C20 cycloalkyloxy, C7-C20 arylalkyl, C6-C20 aryl and C2-C20 heteroaryl. In more preferred embodiment, at least two of $R^6$-$R^{10}$ and at least two of $R^{16}$-$R^{20}$ are methyl, or at least one of $R^6$-$R^{10}$ and at least one of $R^{16}$-$R^{20}$ is selected from C2-C20 alkyl, C3-C20 cycloalkyl, C1-C20 alkoxy, C3-C20 cycloalkyloxy, C7-C20 arylalkyl, C6-C20 aryl and C2-C20 heteroaryl, whereas other $R^6$-$R^{10}$ and $R^{16}$-$R^{20}$ are hydrogen. In an even preferred embodiment, $R^3$ and $R^{13}$ is phenyl and other substituents on $R^3$ and $R^{13}$ bearing phenyl rings are hydrogen atoms. In another preferred embodiment, $R^1$-$R^5$ are the same as $R^{11}$-$R^{15}$ and $R^6$-$R^{10}$ are the same as $R^{16}$-$R^{20}$. In still another preferred embodiment, at least two of $R^6$-$R^{10}$ and at least two of $R^{16}$-$R^{20}$ are methyl, or at least one of $R^6$-$R^{10}$ and at least one of $R^{16}$-$R^{20}$ is selected from C2-C12 alkyl, C3-C12 cycloalkyl. More preferably, $R^8$ and $R^{18}$ is tert-butyl or $R^7$, $R^9$, $R^{17}$ and $R^{19}$ is methyl. For x=1, $R^{21}$ and $R^{22}$ are preferably independently selected from methyl or methoxy.

More preferably, $R^{21}$ and $R^{22}$ are the same. Preferred are also all possible combinations of preferred embodiments mentioned above.

More preferred are the devices comprising embodiments of general structure (I) represented by general formula (II) or (III)

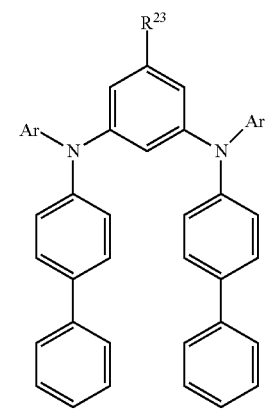

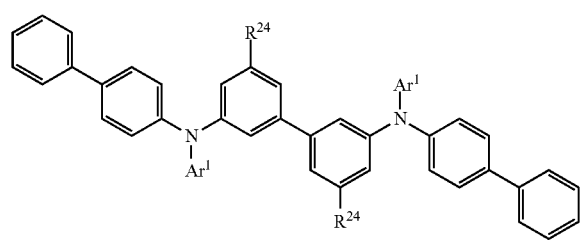

wherein Ar and $Ar^1$ are selected from 4-tert-butylphenyl, 3,5-dimethylphenyl and 2,4,6-trimethylphenyl, $R^{23}$ has the same meaning as $R^{22}$ defined above and $R^{24}$ is hydrogen, C1-C10 alkyl, C3-C10 cycloalkyl, C1-C10 alkoxy and C3-C10 cycloalkyloxy.

Preferably, $R^{23}$ is selected from C2-C20 alkyl, C3-C20 cycloalkyl, C1-C20 alkoxy, C3-C20 cycloalkyloxy, C7-C20 arylalkyl, C6-C20 aryl and C2-C20 heteroaryl. More preferably, $R^{23}$ is selected from the group consisting of methyl, phenyl, 3,5-dimethylphenyl and 1,1'-biphenyl-4-yl. Preferably, $R^{24}$ is C1-C4 alkyl or C1-C4 alkoxy. More preferably, $R^{24}$ is selected from methyl and methoxy.

A further object is achieved by new compounds of general formula (I) as defined above wherein i) at least one of $R^1$-$R^5$ and at least one of $R^{11}$-$R^{15}$ is C6-C20 aryl or C2-C20 heteroaryl or ii) $R^1$ with $R^2$ as well as $R^{11}$ with $R^{12}$ form an aromatic ring or iii) $R^2$ with $R^3$ as well as $R^{12}$ with $R^{13}$ form an aromatic ring;

at least two of $R^6$-$R^{10}$ and at least two of $R^{16}$-$R^{20}$ are methyl, or at least one of $R^6$-$R^{10}$ and at least one of $R^{16}$-$R^{20}$ is selected from C2-C20 alkyl, C3-C20 cycloalkyl, C1-C20 alkoxy, C3-C20 cycloalkyloxy, C7-C20 arylalkyl, C6-C20 aryl and C2-C20 heteroaryl and x is an integer chosen from 0 and 1, wherein for x=0, $R^{22}$ has the same meaning as $R^1$-$R^{20}$ whereas for x=1, $R^{21}$ and $R^{22}$ are independently selected from hydrogen, C1-C10 alkyl, C3-C10 cycloalkyl, C1-C10 alkoxy and C3-C10 cycloalkyloxy.

The alkyl or alkoxy substituent can be saturated or unsaturated, straight or branched. The cycloalkyl or cycloalkoxy substituent may be saturated or unsaturated, monocyclic or polycyclic. The overall C atom count in a substituent includes possible alkyl substitution, branching and/or occurrence of cyclic structures within the substituent. It is advantageous, if the heteroaryl substituent is attached through a carbocyclic ring or through a five-membered heterocyclic ring containing up to three heteroatoms independently chosen from O, N and S. Preferably, the overall C atom count in the compound (I) does not exceed 150. More preferably, the overall C atom count in any group of substituents selected from $R^1$-$R^5$, $R^6$-$R^1$, $R^{11}$-$R^{15}$, $R^{16}$-$R^{20}$, that means of all the substituents bound to one of phenyl rings bound in the structure (I) to nitrogen atoms, does not exceed 20. Most preferably, the overall C atom count in any group of substituents selected from $R^1$-$R^5$, $R^6$-$R^1$, $R^{11}$-$R^{15}$, $R^{16}$-$R^{20}$ does not exceed 12.

More preferably, this object is achieved by new compounds of general formula (I) wherein
i) at least one of $R^1$-$R^5$ and at least one of $R^{11}$-$R^{15}$ is C6-C20 aryl or C2-C20 heteroaryl or
ii) $R^1$ with $R^2$ as well as $R^{11}$ with $R^{12}$ form an aromatic ring or
iii) $R^2$ with $R^3$ as well as $R^{12}$ with $R^{13}$ form an aromatic ring
and
at least two of $R^6$-$R^{10}$ and at least two of $R^{16}$-$R^{20}$ are methyl, or at least one of $R^6$-$R^{10}$ and at least one of $R^{16}$-$R^{20}$ is selected from C2-C20 alkyl, C3-C20 cycloalkyl, C1-C20 alkoxy, C3-C20 cycloalkyloxy, C7-C20 arylalkyl, C6-C20 aryl and C2-C20 heteroaryl, whereas other $R^6$-$R^{10}$ and $R^{16}$-$R^{20}$ are H.

Even preferably, this object is achieved by new compounds of general formula (I) wherein
at least one of $R^1$-$R^5$ and at least one of $R^{11}$-$R^{15}$ is C6-C20 aryl or C2-C20 heteroaryl;
at least two of $R^6$-$R^{10}$ and at least two of $R^{16}$-$R^{20}$ are methyl, or
at least one of $R^6$-$R^{10}$ and at least one of $R^{16}$-$R^{20}$ is selected from C2-C20 alkyl, C3-C20 cycloalkyl, C1-C20 alkoxy, C3-C20 cycloalkyloxy, C7-C20 arylalkyl, C6-C20 aryl and C2-C20 heteroaryl,
whereas other $R^1$-$R^5$, $R^6$-$R^{10}$, $R^{11}$-$R^{15}$ and $R^{16}$-$R^{20}$ are H.

Even more preferably, this object is achieved by new compounds of general formula (I) wherein
at least one of $R^1$-$R^5$ and at least one of $R^{11}$-$R^{15}$ is phenyl;
at least two of $R^6$-$R^{10}$ and at least two of $R^{16}$-$R^{20}$ are methyl, or
at least one of $R^6$-$R^{10}$ and at least one of $R^{16}$-$R^{20}$ is selected from C2-C20 alkyl, C3-C20 cycloalkyl, C1-C20 alkoxy, C3-C20 cycloalkyloxy, C7-C20 arylalkyl, C6-C20 aryl and C2-C20 heteroaryl,
whereas other $R^1$-$R^5$, $R^6$-$R^{10}$, $R^{11}$-$R^{15}$ and $R^{16}$-$R^{20}$ are H.

Even more preferably, this object is achieved by new compounds of general formula (II) or (III) defined above, most preferably in their embodiments preferred above.

It is preferred that at least one layer containing the compound of formula (I) is electrically doped.

More preferably, the layer containing the compound of formula (I) has at least one doped portion and at least one portion which is less doped than the doped portion or is un-doped. In this embodiment, the less doped or undoped part of the layer serves as electron blocking layer.

In one yet preferred embodiment, the undoped part of the layer serves as both electron-blocking and triplet exciton blocking layer.

DETAILED DESCRIPTION OF THE INVENTION

In a research striving to find new ways to approaching better OLEDs, it was surprisingly found by the authors that certain hole-transporting materials known for long, like

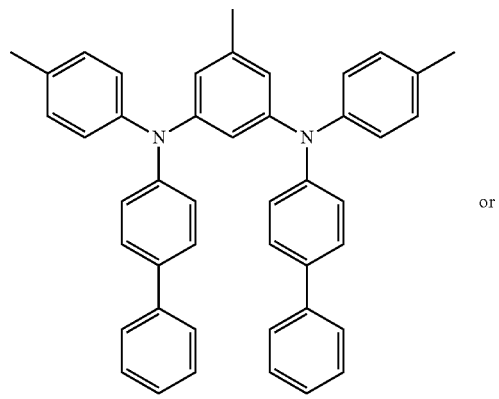

or

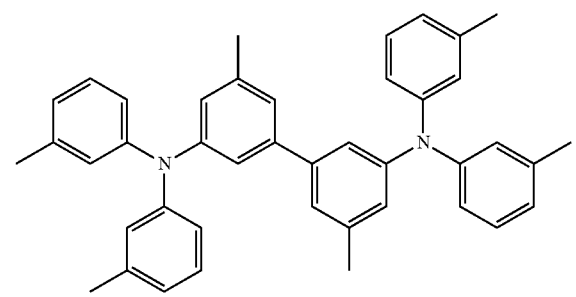

perform unexpectedly well when used in OLEDs comprising a phosphorescent emitter, whereas their performance in conventional fluorescent OLEDS is only moderate and no way achieves the level provided by established hole transporting matrix materials like

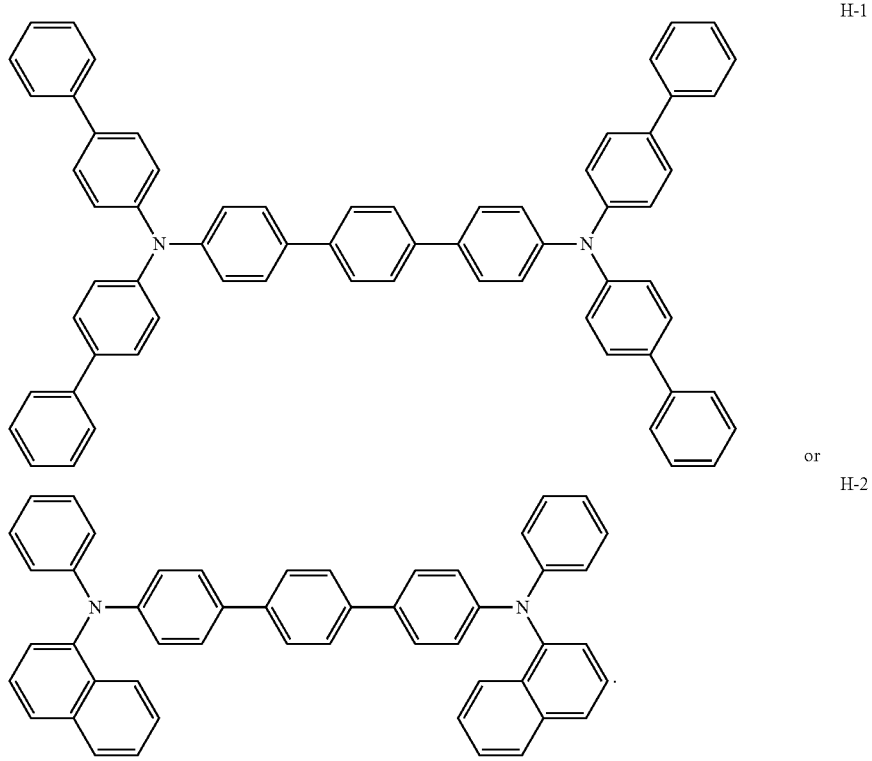

Further research helped clarifying relationships with the structure of the compounds tested and confirmed that the improvement is rather general. Table 1 shows the experimental results obtained by the procedure described in detail in the examples below. In the experimental OLEDs tested, the hole transporting layer was doped with a p-dopant, what is symbolized with the p-symbol in the substrate/HTL/EBL column. In the table, to the compounds showing voltage lower voltage than reference, negative values were assigned in the voltage column. Oppositely, a positive value in the voltage column shows unfavourable, higher average voltage observed at the set of devices comprising inventive compound in comparison with the average voltage measured on the set of reference devices prepared under the same conditions. In the efficiency column, the average efficiency of devices comprising an inventive compound higher than the average efficiency of comparative devices is positive, whereas unfavourable lower efficiency in comparison with reference has negative sign. The last column in the table shows the arithmetic difference between the value in the efficiency column and the value in the voltage column. The resulting value was used as a benchmark for assessing the overall performance. Its positive value in at least one from the three rows shows that at least in one application—if the compound was used as an EBL, as an HTL, or in both layers—shows that in this particular case, the percentage voltage improvement has overweighed the percentage efficiency decrease or, oppositely, that the percentage efficiency improvement overweighed the undesired voltage increase, or that there was an improvement in both properties. In fluorescent blue OLED, there was uniformly no particular (in at least one—efficiency or voltage—value) improvement at all for all compounds tested. Consequently, all overall performance values were strongly negative. Surprisingly, in the phosphorescent OLED, the only combination of the structural features of the substituents tested which unequivocally failed (afforded negative overall performance in all applications) was the $R^{23}$ substituent defined as phenyl bearing at least one strongly electron withdrawing group. The gained knowledge was exploited for providing new hole transporting and electron-blocking matrix materials, particularly useful in OLEDs comprising triplet emitters.

TABLE 1

| | | | | phosphorescent green | | |
|---|---|---|---|---|---|---|
| Compound tested | Core substit. | Periphery s. | substrate/HTL/EBL | voltage change [%] | Q eff change [%] | Q − voltage [%] |
| | | | ITO/p-H-1/H-2 | −8 | −49 | −41 |
| | | | ITO/p-H-2/H-2 | −8 | −50 | −42 |
| | | | ITO/p-H-1/TCTA | | 0 | |
| | | | ITO/p-TCTA/TCTA | +38 | +5 | |
| | | | ITO/p-H-1/MPD-1 | −6 | −5 | 1 |
| | | | ITO/p-MPD-1/TCTA | +6 | +15 | 9 |
| | | | ITO/p-MPD-1/MPD-1 | −4 | +11 | 15 |

TABLE 1-continued

| Compound tested | Core substit. | Periphery s. | substrate/HTL/EBL | phosphorescent green voltage change [%] | Q eff change [%] | Q – voltage [%] |
|---|---|---|---|---|---|---|
| | | | ITO/p-H-1/MPD-2 | −7 | −47 | −40 |
| | | | ITO/p-MPD-2/TCTA | +1 | +7 | 6 |
| | | | ITO/p-MPD-2/MPD-2 | −5 | −44 | −39 |
| | | | ITO/p-H-1/MPD-3 | −4 | −46 | −42 |
| | | | ITO/p-MPD-3/TCTA | −1 | +6 | 7 |
| | | | ITO/p-MPD-3/MPD-3 | −3 | −40 | −37 |
| | | | ITO/p-H-1/MPD-4 | −6 | −4 | 2 |
| | | | ITO/p-MPD-4/TCTA | +1 | +12 | 11 |
| | | | ITO/p-MPD-4/MPD-4 | −5 | 0 | 5 |
| | | | ITO/p-H-1/MPD-5 | −6 | +1 | 7 |
| | | | ITO/p-MPD-5/TCTA | +5 | +13 | 8 |
| | | | ITO/p-MPD-5/MPD-5 | −5 | +13 | 18 |
| | | | ITO/p-H-1/MPD-6 | −4 | 0 | 4 |
| | | | ITO/p-MPD-6/TCTA | +5 | +14 | 9 |
| | | | ITO/p-MPD-6/MPD-6 | −3 | +13 | 16 |
| | | | ITO/p-H-1/MPD-7 | −8 | −15 | −7 |
| | | | ITO/p-MPD-7/TCTA | +4 | +10 | 6 |
| | | | ITO/p-MPD-7/MPD-7 | −5 | −4 | 1 |
| | | | ITO/p-H-1/MPD-8 | −7 | −9 | −2 |
| | | | ITO/p-MPD-8/TCTA | +10 | +13 | 3 |
| | | | ITO/p-MPD-8/MPD-8 | +2 | +3 | 1 |
| | | | ITO/p-H-1/MPD-9 | −6 | −6 | 0 |
| | | | ITO/p-MPD-9/TCTA | +6 | +16 | 10 |
| | | | ITO/p-MPD-9/MPD-9 | −5 | +9 | 14 |
| | | | ITO/p-H-1/MPD-10 | +3 | +4 | 1 |
| | | | ITO/p-MPD-10/TCTA | +14 | +20 | 6 |
| | | | ITO/p-MPD-10/MPD-10 | +18 | +16 | −2 |
| | | | ITO/p-H-1/MPD-11 | +8 | −7 | −15 |
| | | | ITO/p-MPD-11/TCTA | +18 | +6 | −12 |
| | | | ITO/p-MPD-11/MPD-11 | +30 | +3 | −27 |
| | | | ITO/p-H-1/MPD-12 | −5 | −2 | 3 |
| | | | ITO/p-MPD-12/TCTA | +16 | +14 | −2 |
| | | | ITO/p-MPD-12/MPD-12 | +8 | +12 | 4 |
| | | | ITO/p-H-1/MPD-13 | −7 | −5 | 2 |
| | | | ITO/p-MPD-13/TCTA | −7 | −5 | 2 |
| | | | ITO/p-MPD-13/MPD-13 | −5 | +8 | 13 |
| | | | ITO/p-H-1/MPD-14 | −8 | −13 | −5 |
| | | | ITO/p-MPD-14/TCTA | +2 | +12 | 10 |
| | | | ITO/p-MPD-14/MPD-14 | −6 | −5 | 1 |
| | | | ITO/p-H-1/MPD-15 | −7 | −16 | −9 |
| | | | ITO/p-MPD-15/TCTA | +1 | +9 | 8 |
| | | | ITO/p-MPD-15/MPD-15 | −4 | −9 | −5 |
| | | | ITO/p-H-1/MDAB-1 | −4 | 0 | 4 |
| | | | ITO/p-MDAB-1/TCTA | +6 | +14 | 8 |
| | | | ITO/p-MDAB-1/MDAB-1 | −2 | +12 | 14 |
| | | | ITO/p-H-1/MDAB-2 | −5 | −1 | 4 |
| | | | ITO/p-MDAB-2/TCTA | +8 | +14 | 6 |
| | | | ITO/p-MDAB-2/MDAB-2 | −2 | +13 | 15 |
| | | | ITO/p-H-1/MDAB-3 | −6 | −5 | 1 |
| | | | ITO/p-MDAB-3/TCTA | +2 | +6 | 4 |
| | | | ITO/p-MDAB-3/MDAB-3 | −4 | +4 | 8 |
| | | | ITO/p-H-1/MDAB-4 | −4 | −3 | 1 |
| | | | ITO/p-MDAB-4/TCTA | +13 | +8 | −5 |
| | | | ITO/p-MDAB-4/MDAB-4 | +15 | +7 | −8 |
| | | | ITO/p-H-1/MDAB-5 | −2 | +1 | 3 |
| | | | ITO/p-MDAB-5/TCTA | +19 | +7 | −12 |
| | | | ITO/p-MDAB-5/MDAB-5 | +19 | +8 | −11 |

Additionally, it has been found that inventive compounds are advantageous also when used as hole transporting and/or electron blocking matrices in blue fluorescent OLEDs.

Emitting layer, electron transporting layer, hole blocking layer, electrodes Other parts of the inventive phosphorescent light emitting device than the inventive hole transporting and/or electron blocking layer can be prepared in various designs and from various materials described in the scientific and patent literature.

In the examples, following supporting materials were used:

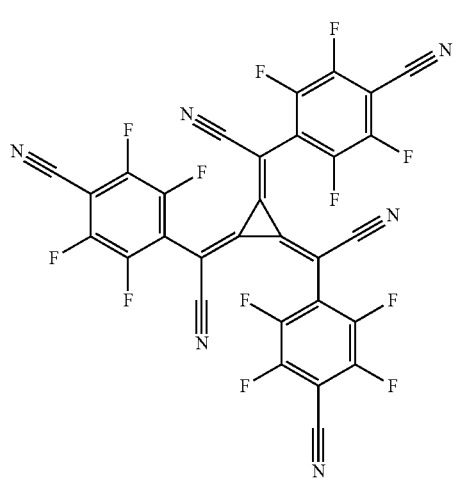

as a p-dopant,

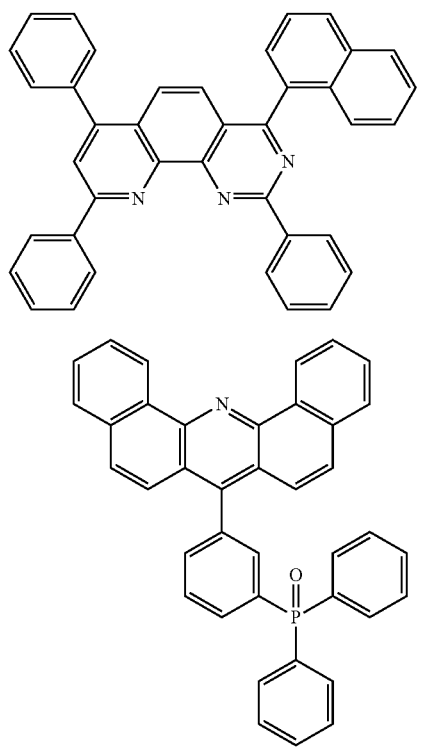

as electron-transporting matrices,

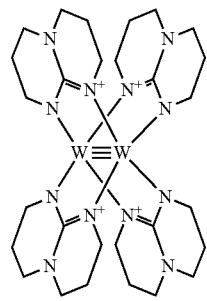

as n dopant,

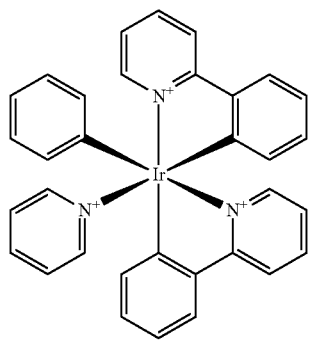

as the triplet emitter,

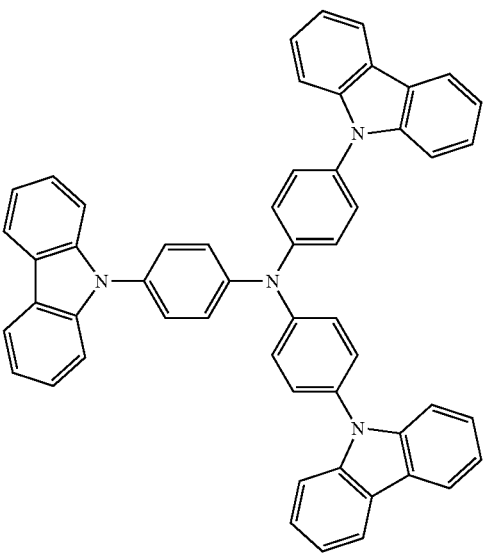

as a known electron blocking matrix.

EXAMPLES

Figure 1:
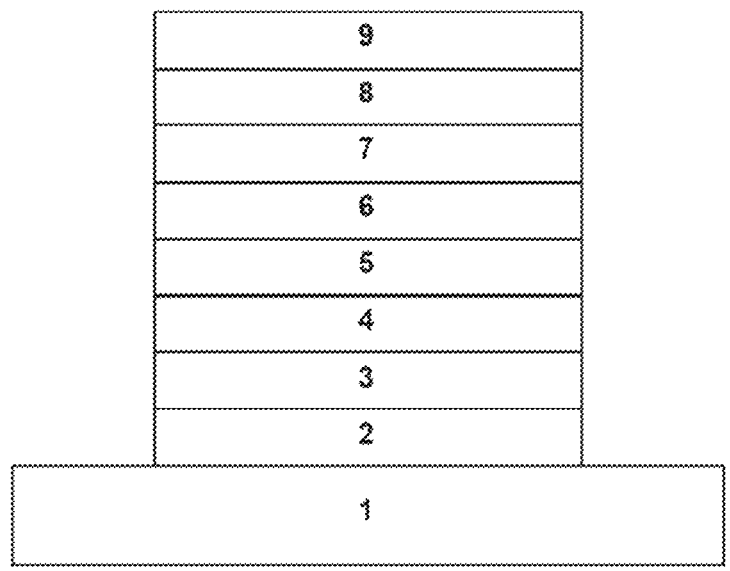
FIG. 1: Schematic drawing of experimental bottom emitting phosphorescent OLED
Figure 2:
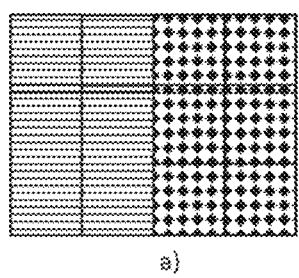
FIG. 2: a) Top view of deposition of layer 1 (p-doped inventive material (stripes), p-doped reference (dots), left; b) Top view of layer 2 after rotation of substrate by 90°, with the inventive material in the top row (fields A, C) and reference material in the bottom row (fields B, D).
Figure 2:
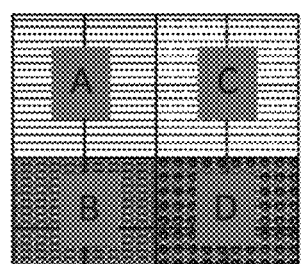
Figure 3A:
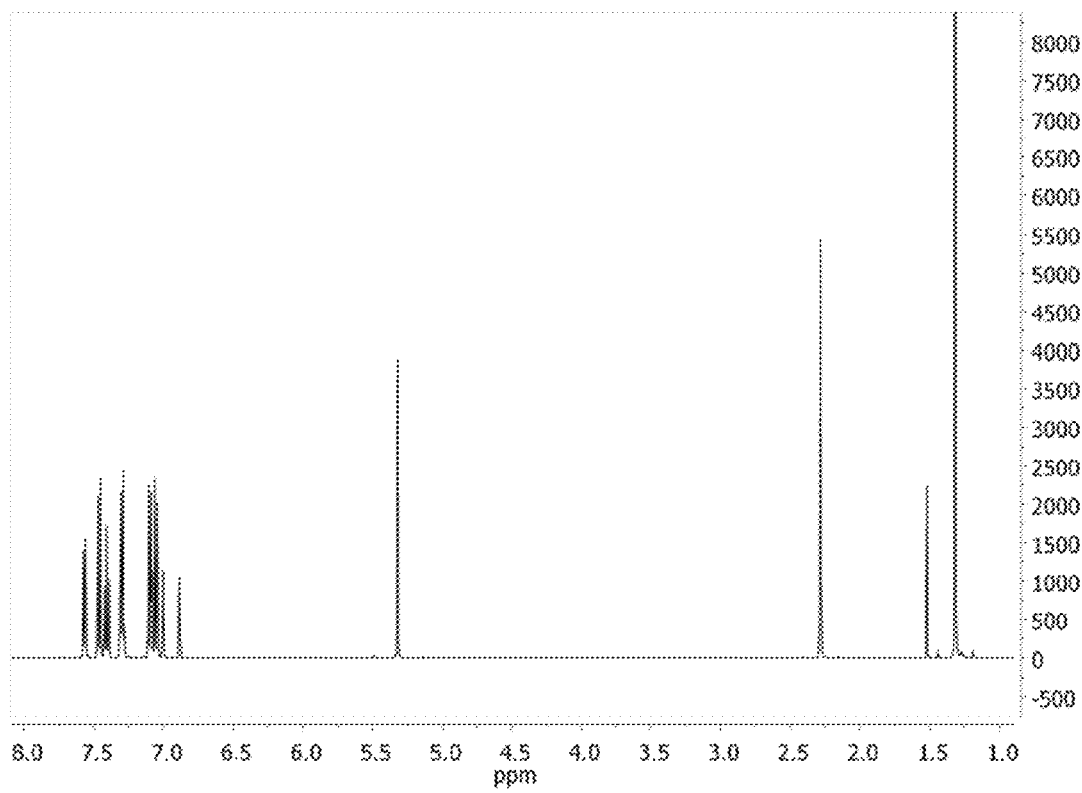
FIG. 3a—3g: $^1$H-NMR spectra of example compounds having formula (II) measured in $CD_2Cl_2$ solution, at 500.13 MHz, referenced to 5.31 ppm; 3a—MDAB-1, 3b—MDAB-2, 3c—MDAB-3, 3d—MDAB-4, 3e—MDAB-5, 3f—MDAB-6, 3g—MDAB-7.
Figure 3B:
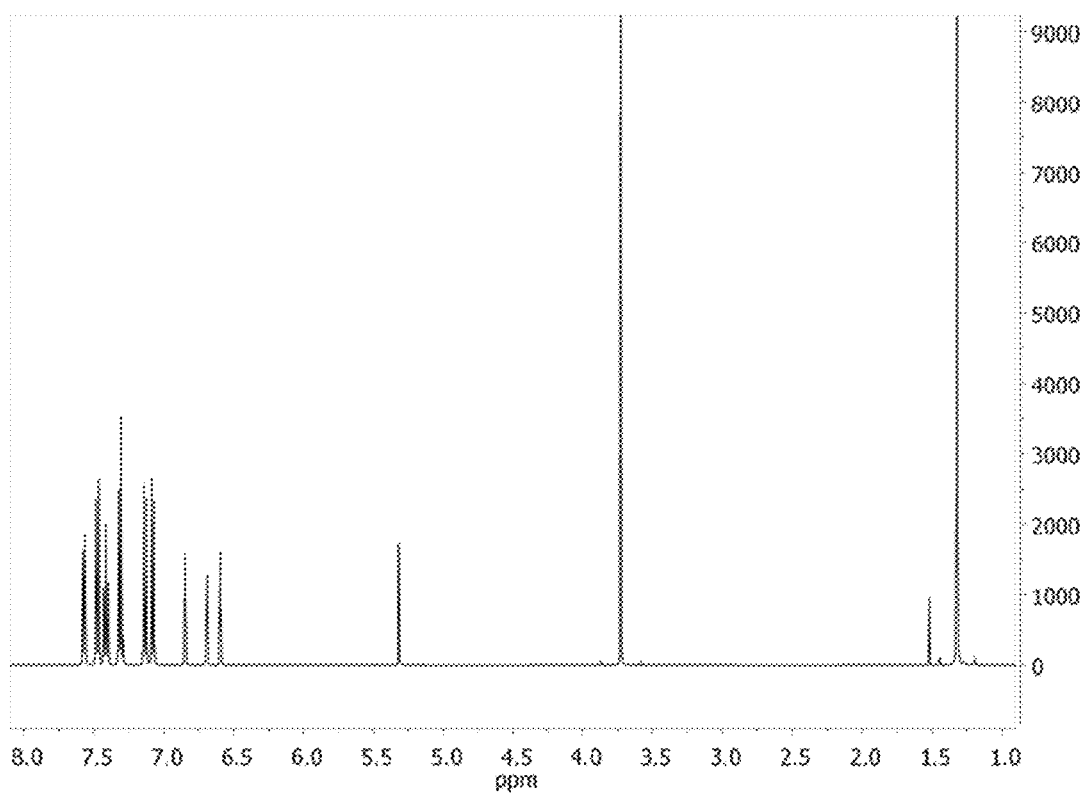
Figure 3C:
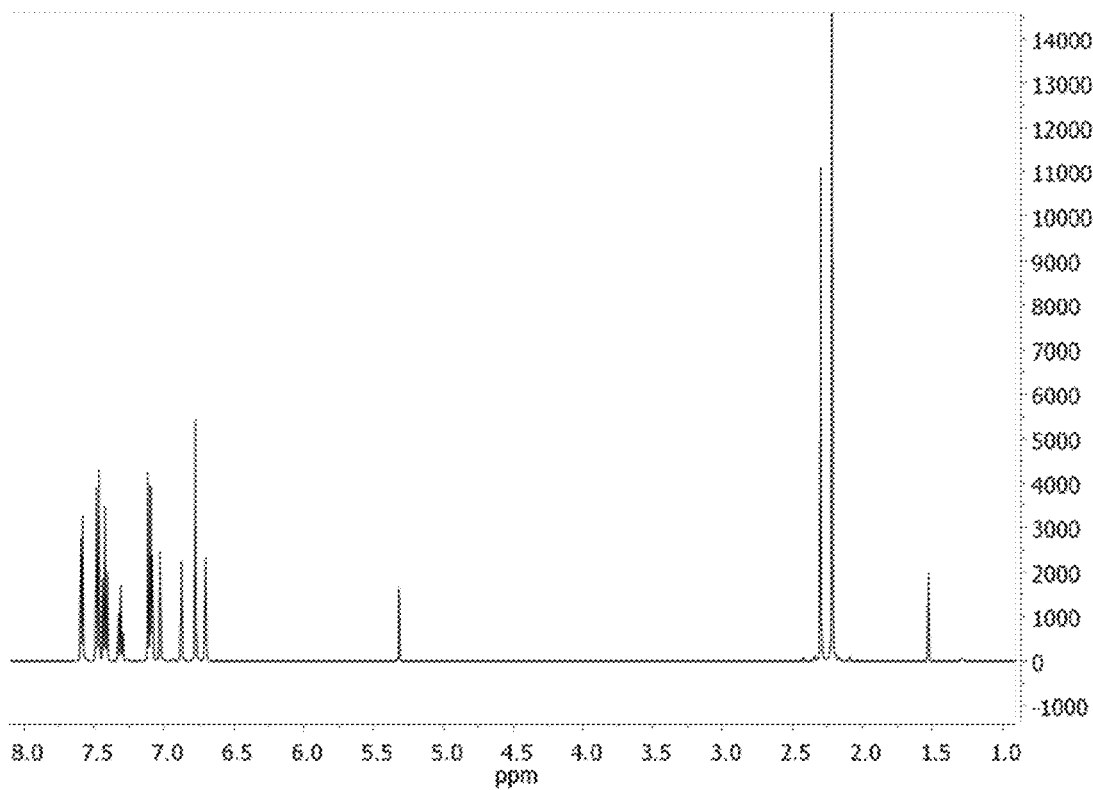
Figure 3D:
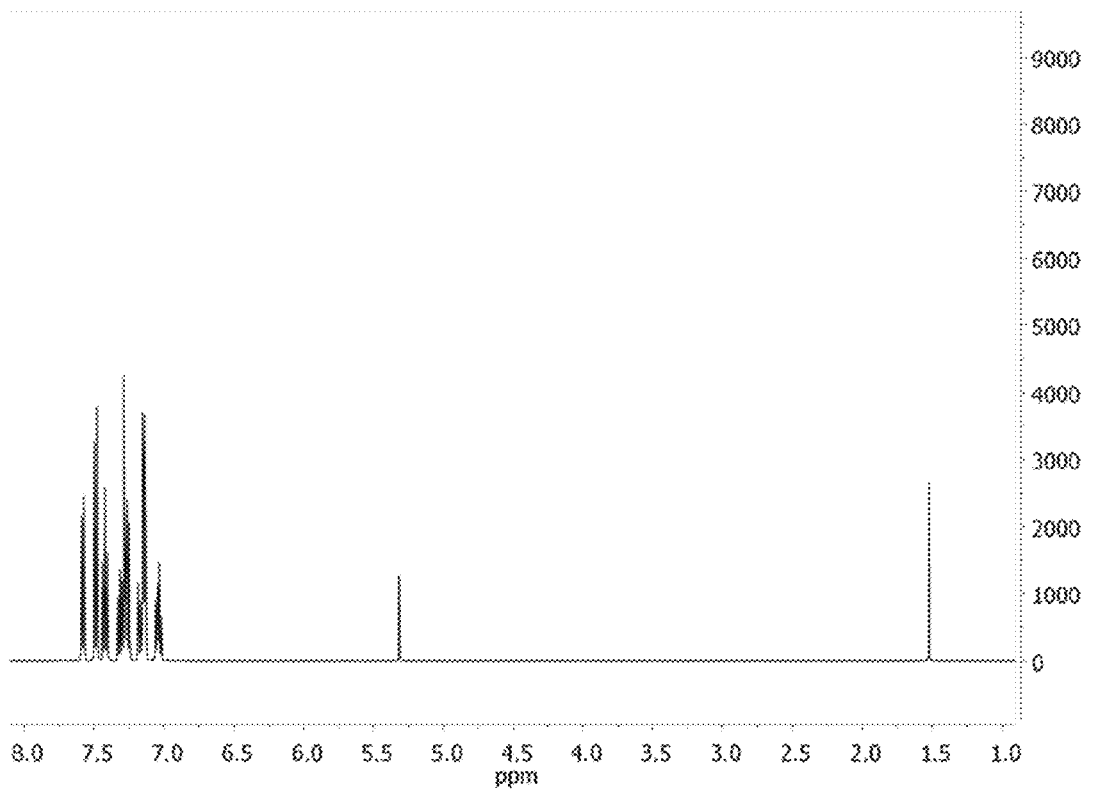
Figure 3E:
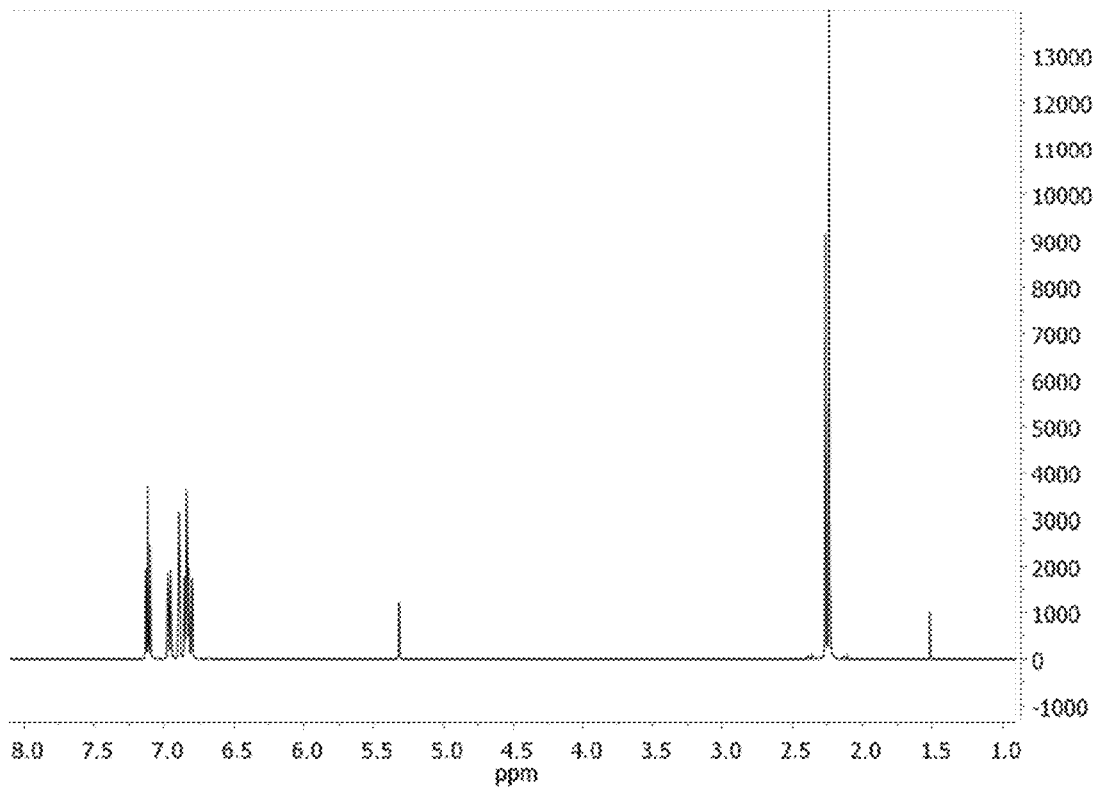
Figure 3F:
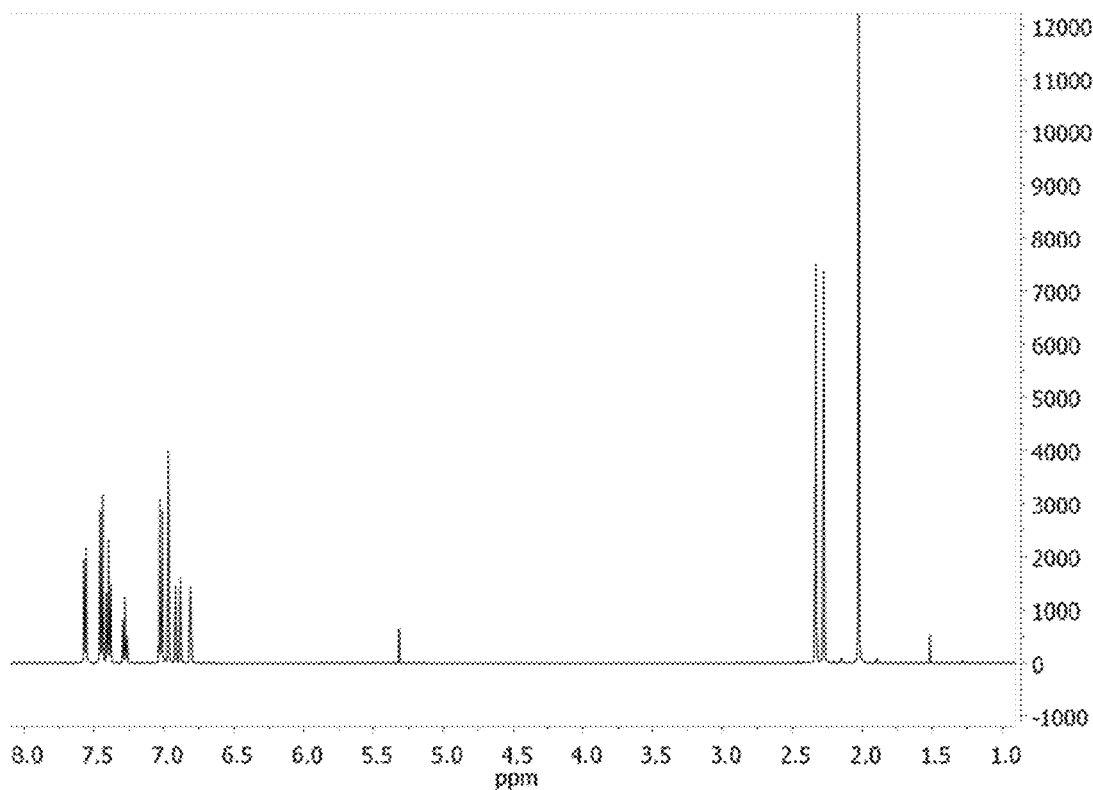
Figure 3G:
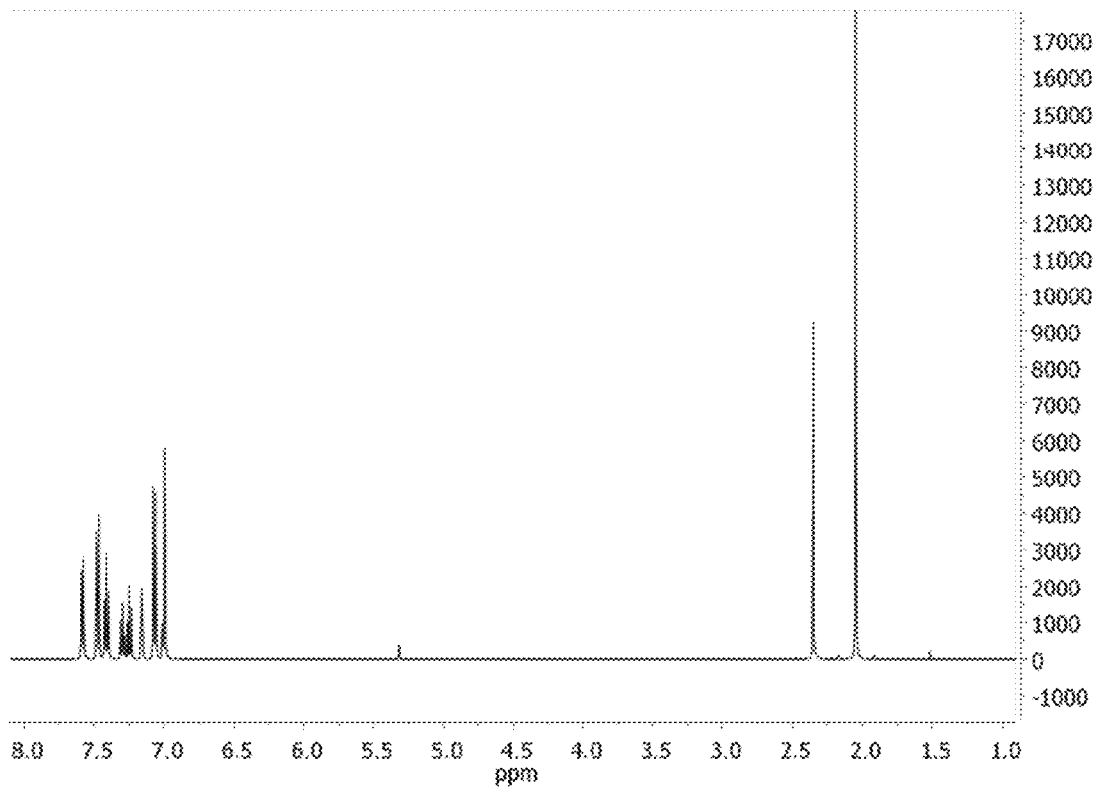
Figure 4A:
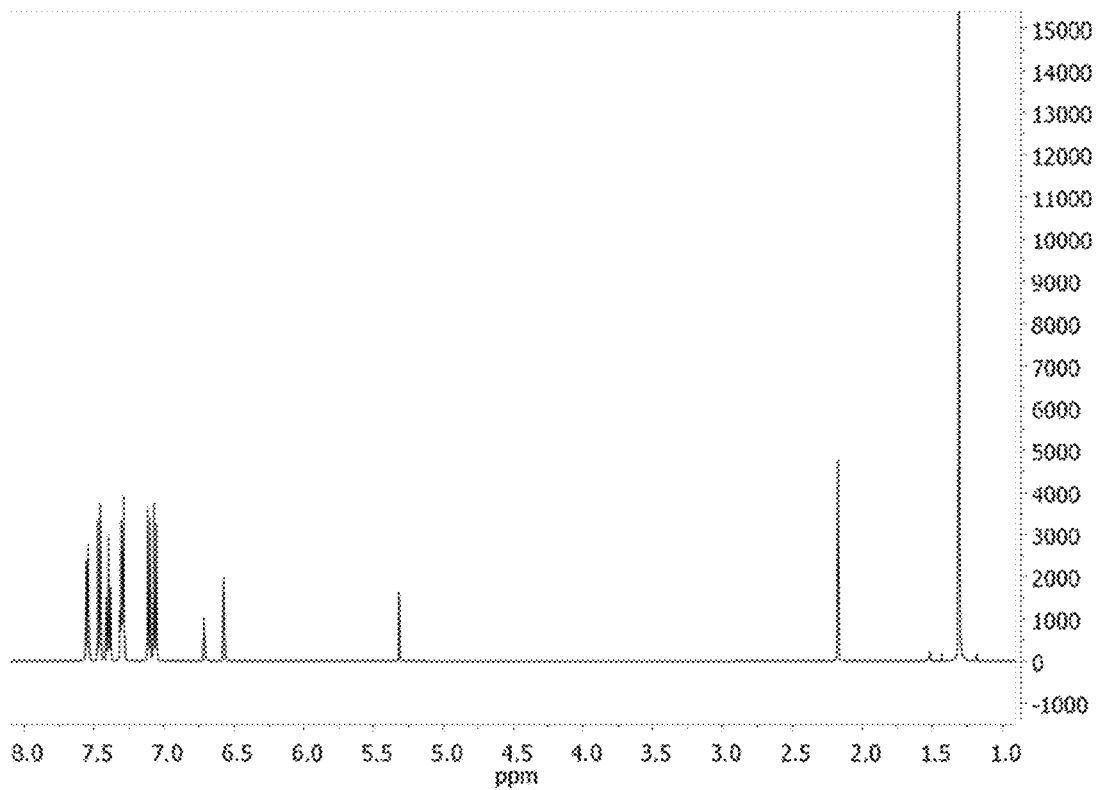
FIG. 4a—4o: $^1$H-NMR spectra of example compounds having formula (III) measured under the same conditions; 4a—MPD-1, 4b—MPD-2, 4c—MPD-3, 4d—MPD-4, 4e—MPD-5, 4f—MPD-6, 4g—MPD-7, 4h—MPD-8, 4i—MPD-9, 4j—MPD-10, 4k—MPD-11, 4l—MPD-12, 4m-MPD-13, 4n—MPD-14, 4o—MPD-15.
Figure 4B:
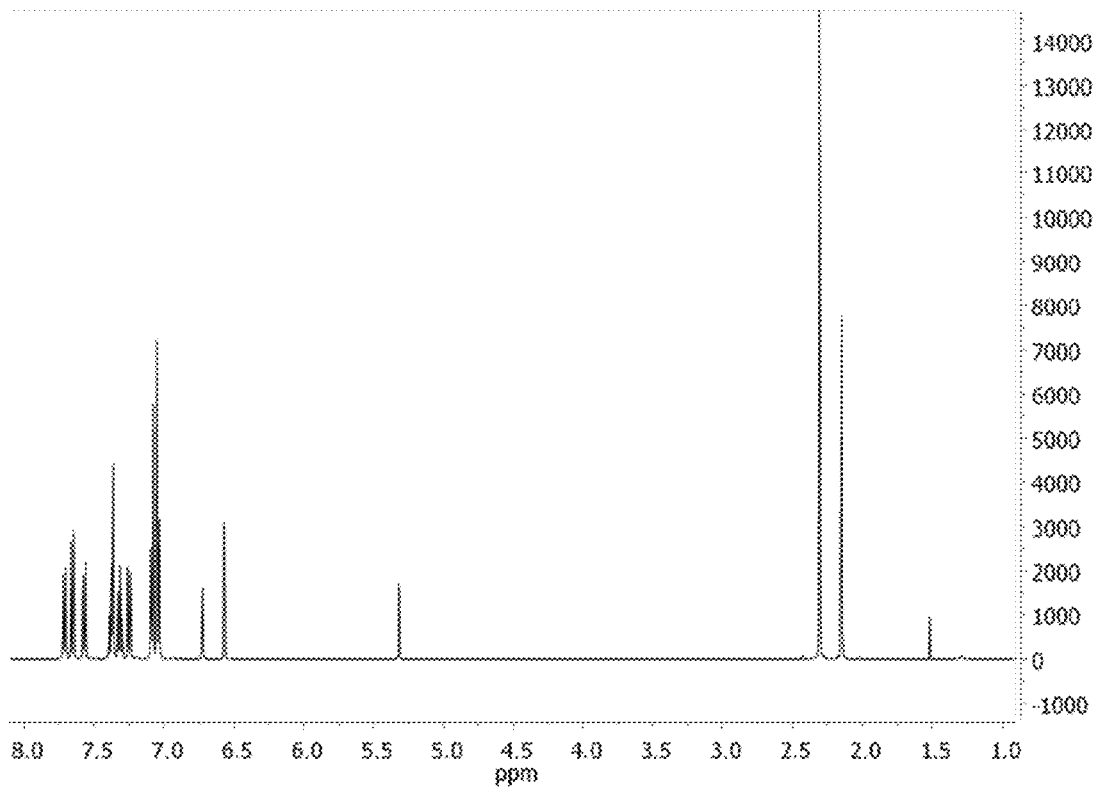
Figure 4C:
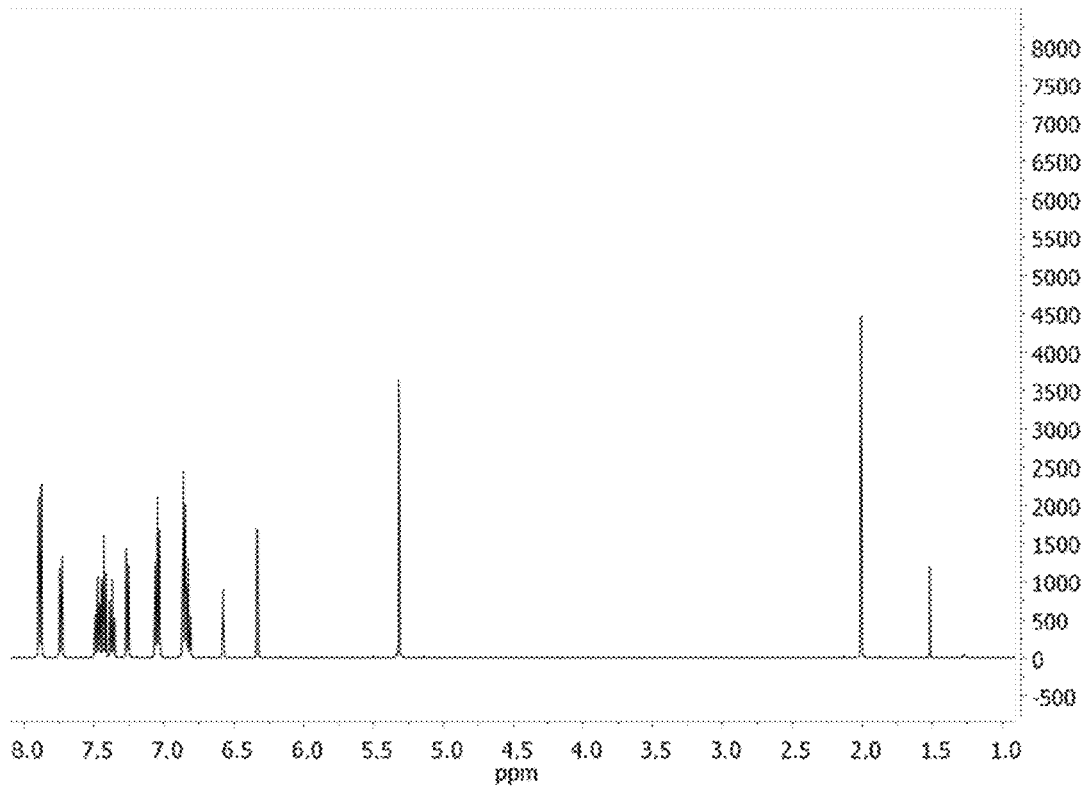
Figure 4D:
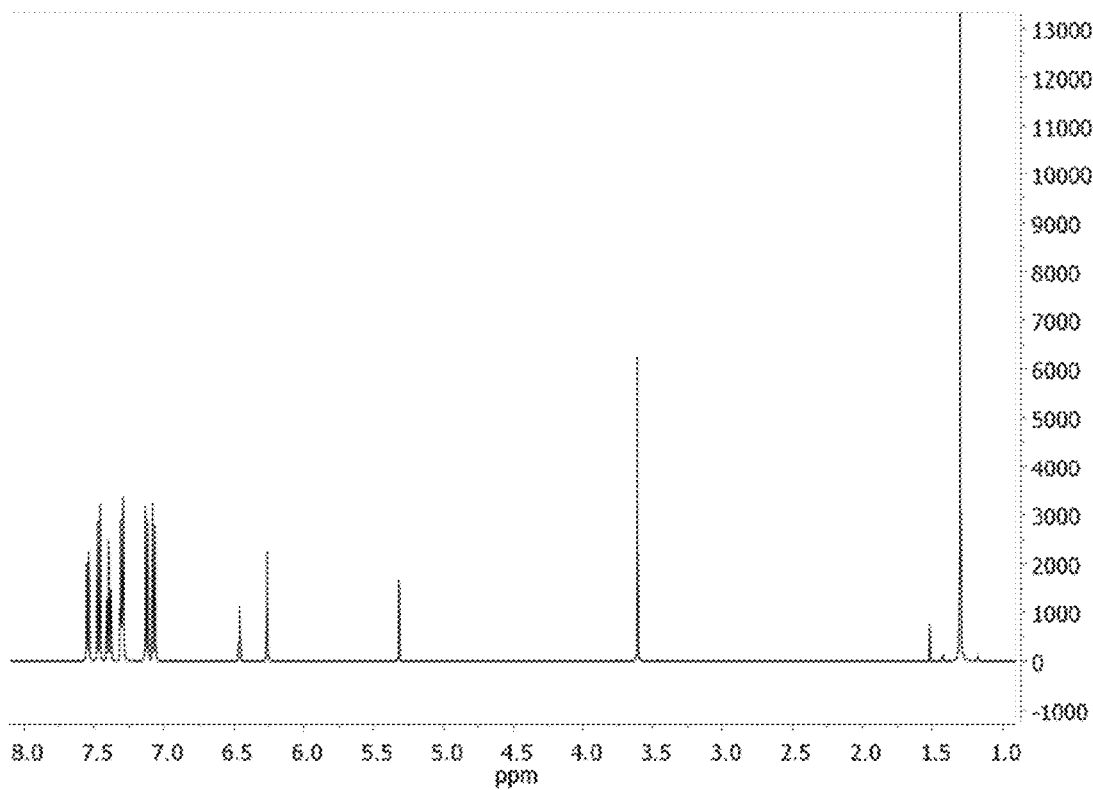
Figure 4E:
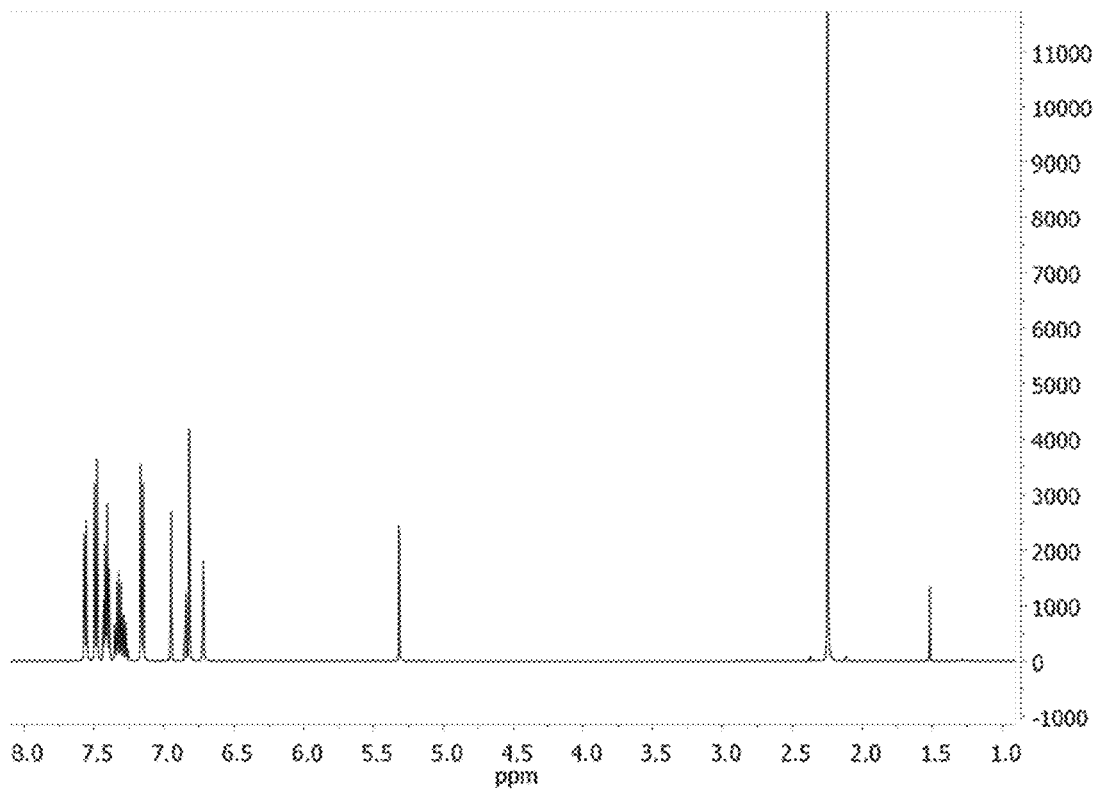
Figure 4F:
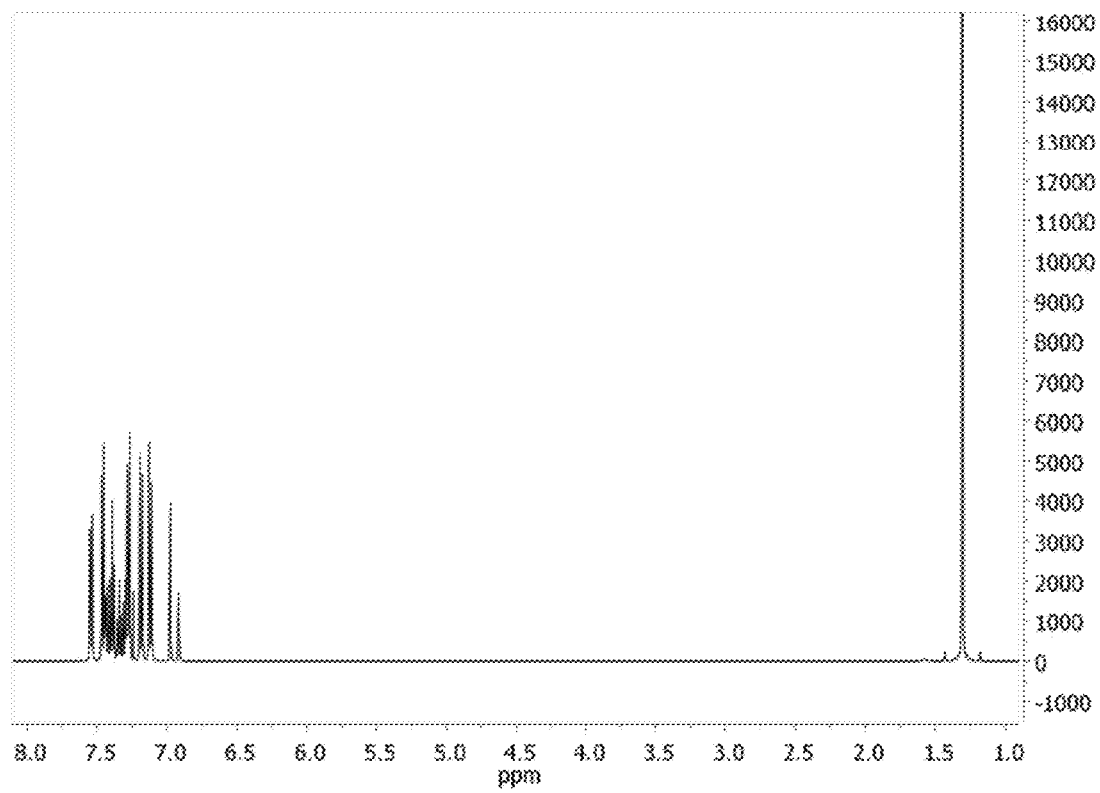
Figure 4G:
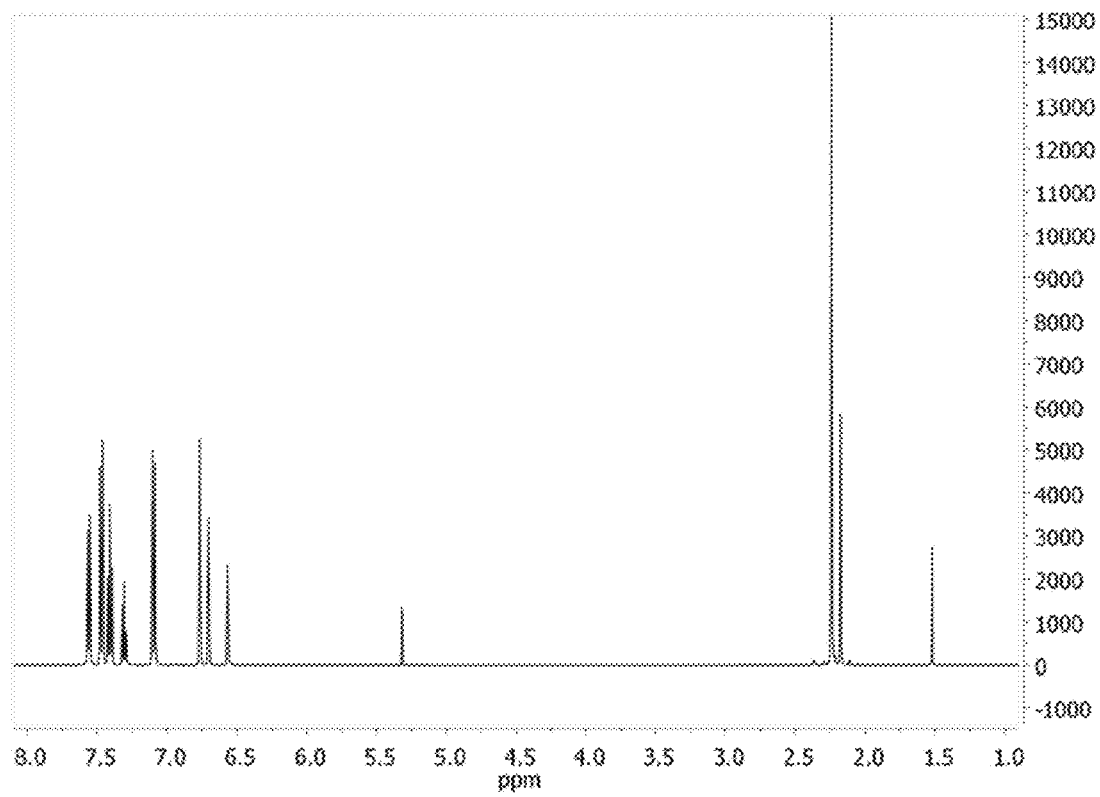
Figure 4H:
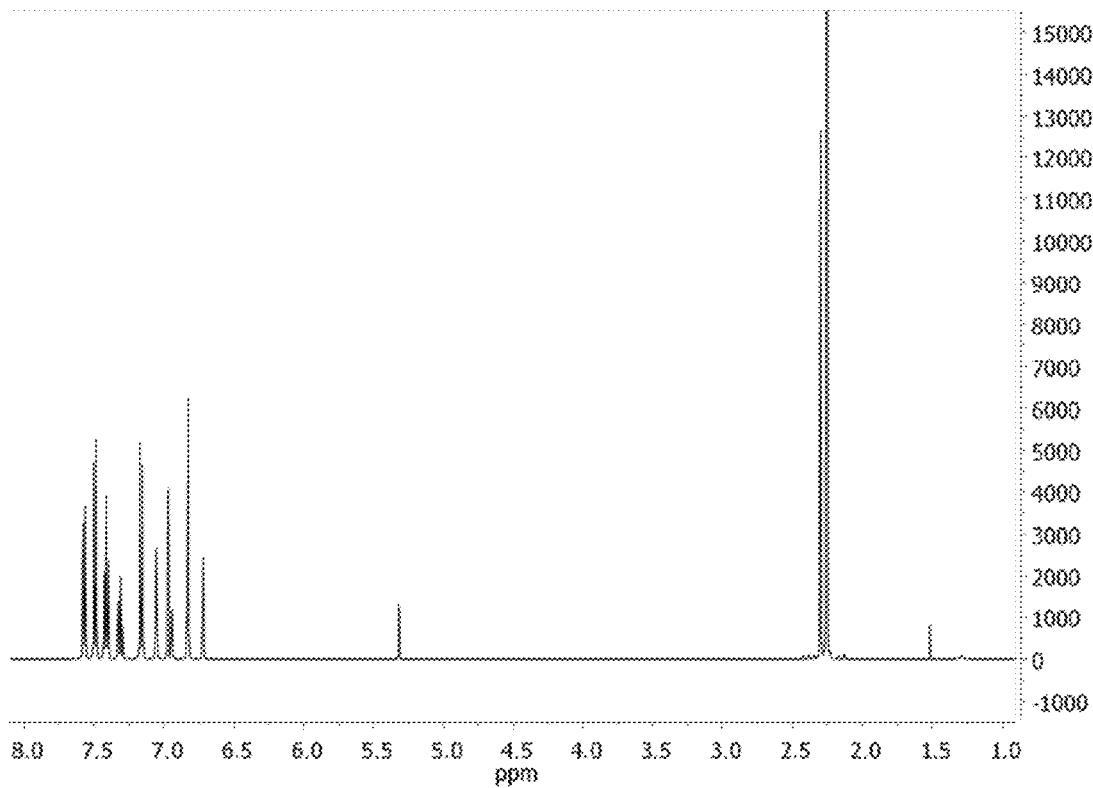
Figure 4I:
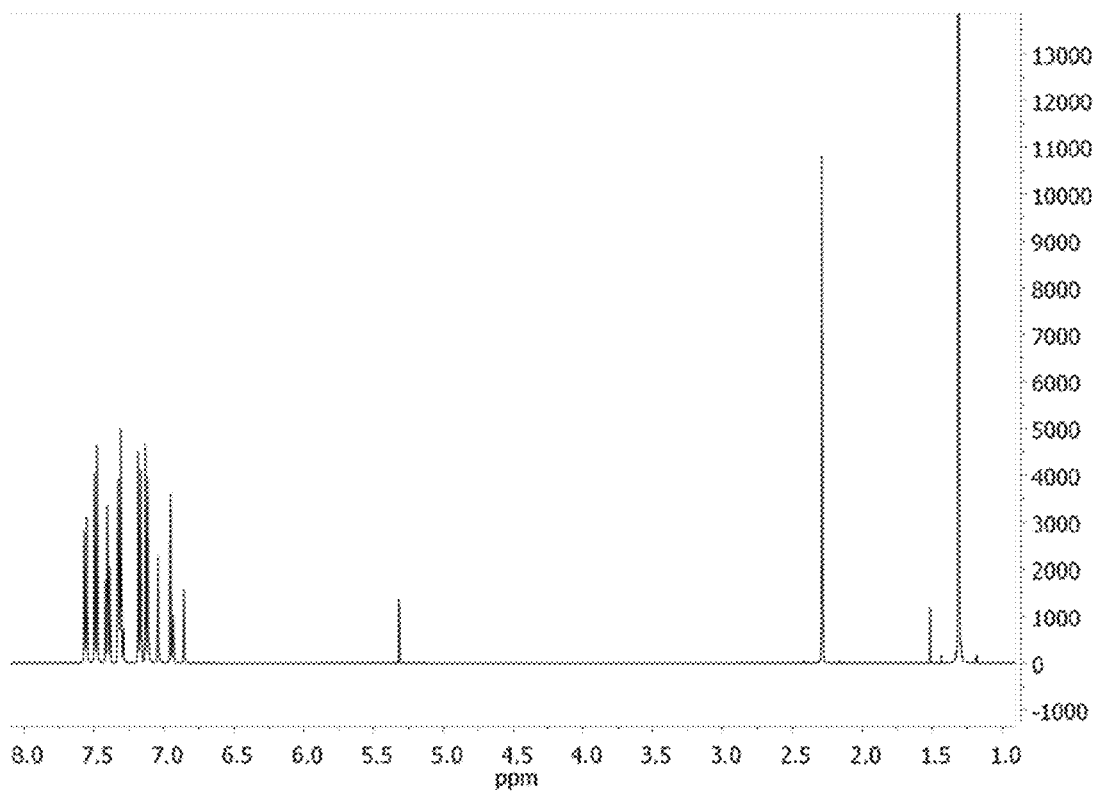
Figure 4J:
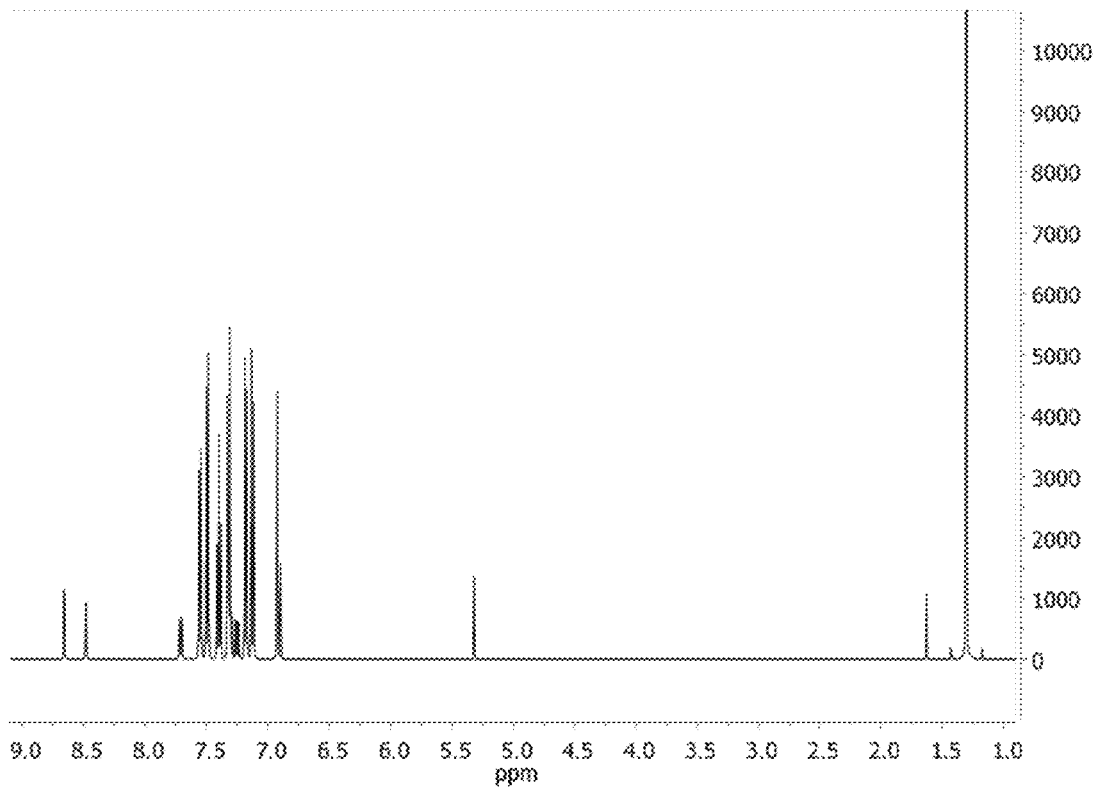
Figure 4K:
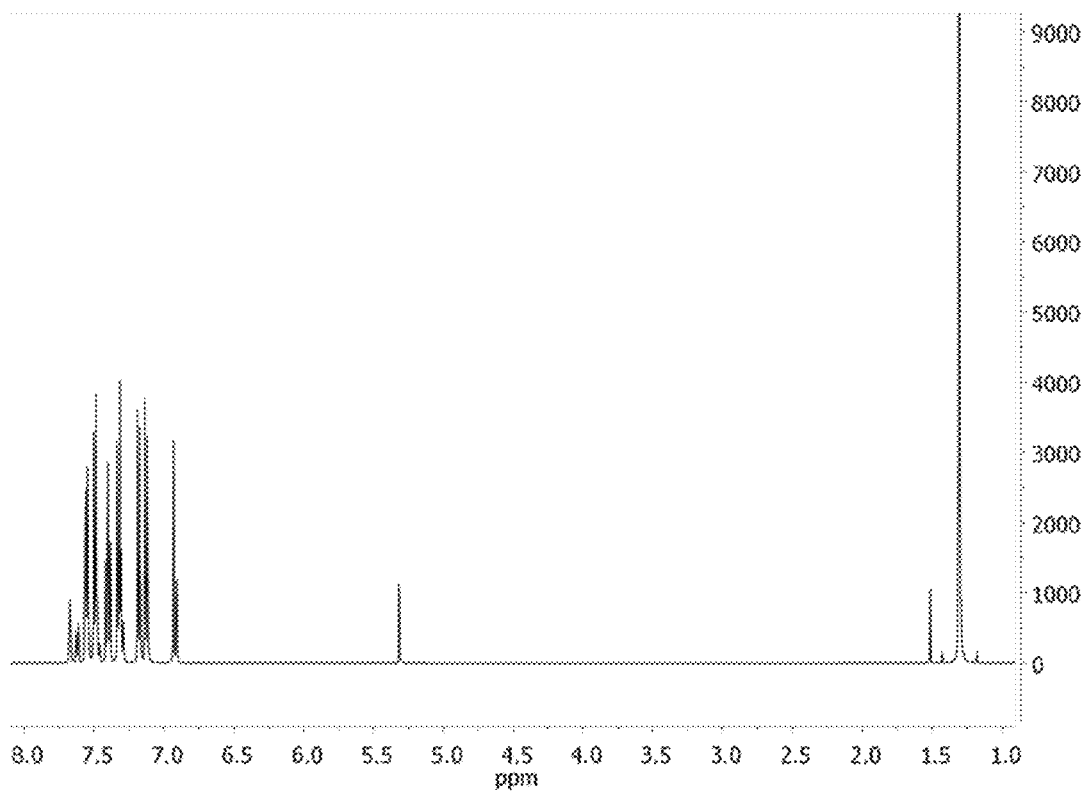
Figure 4L:
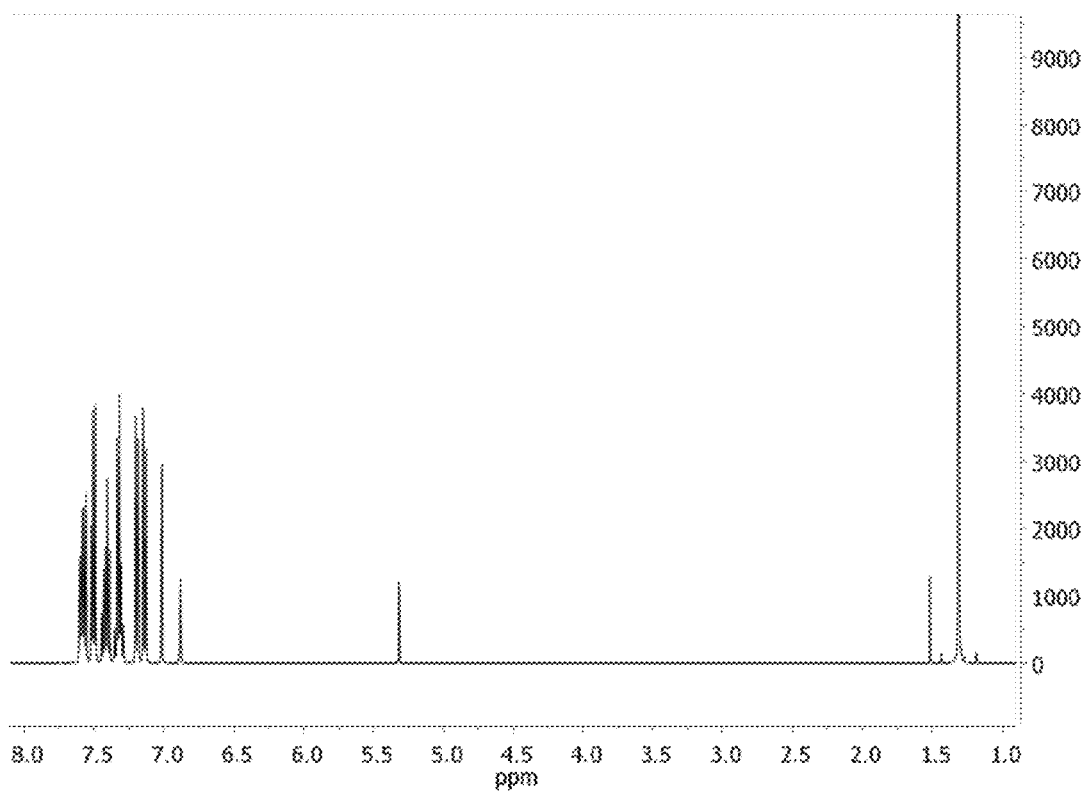
Figure 4M:
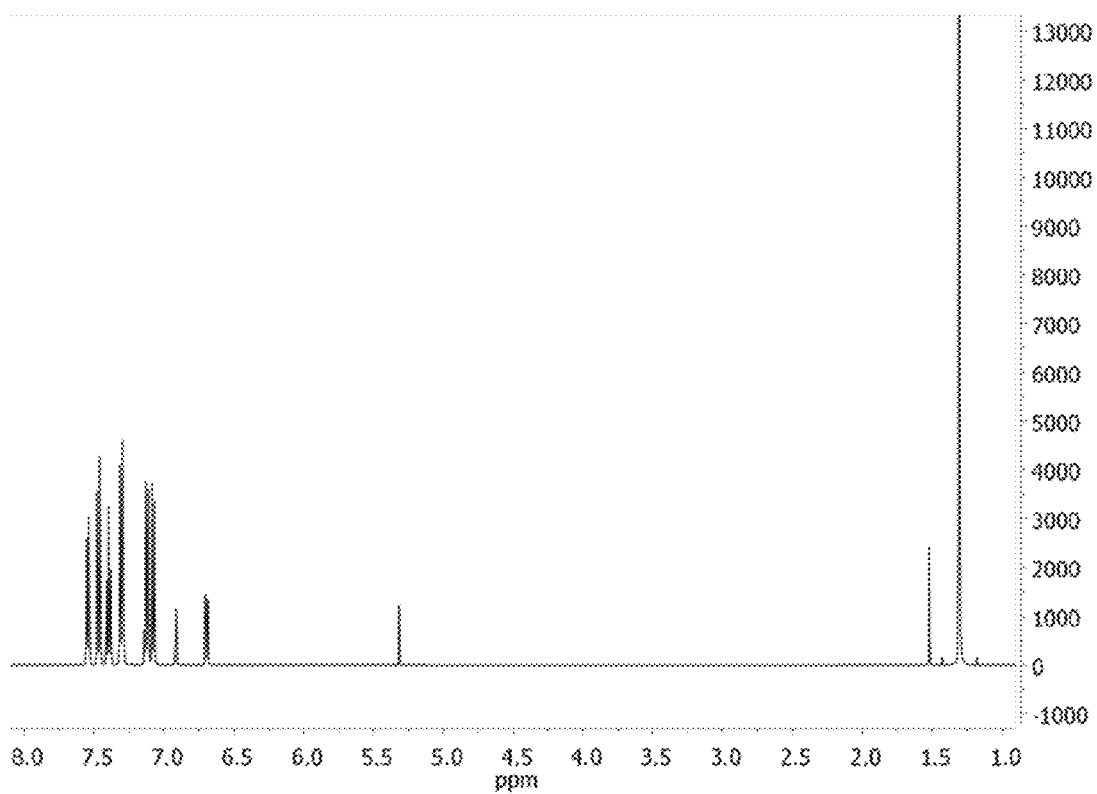
Figure 4N:
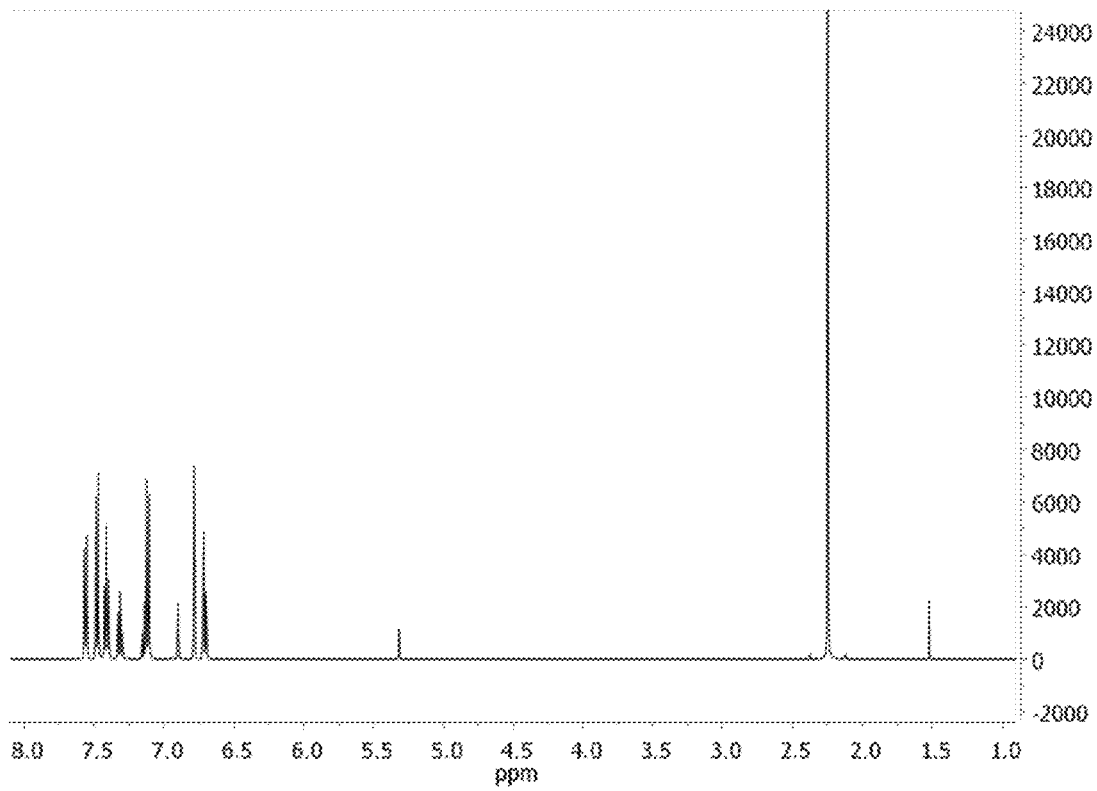
Figure 4O:
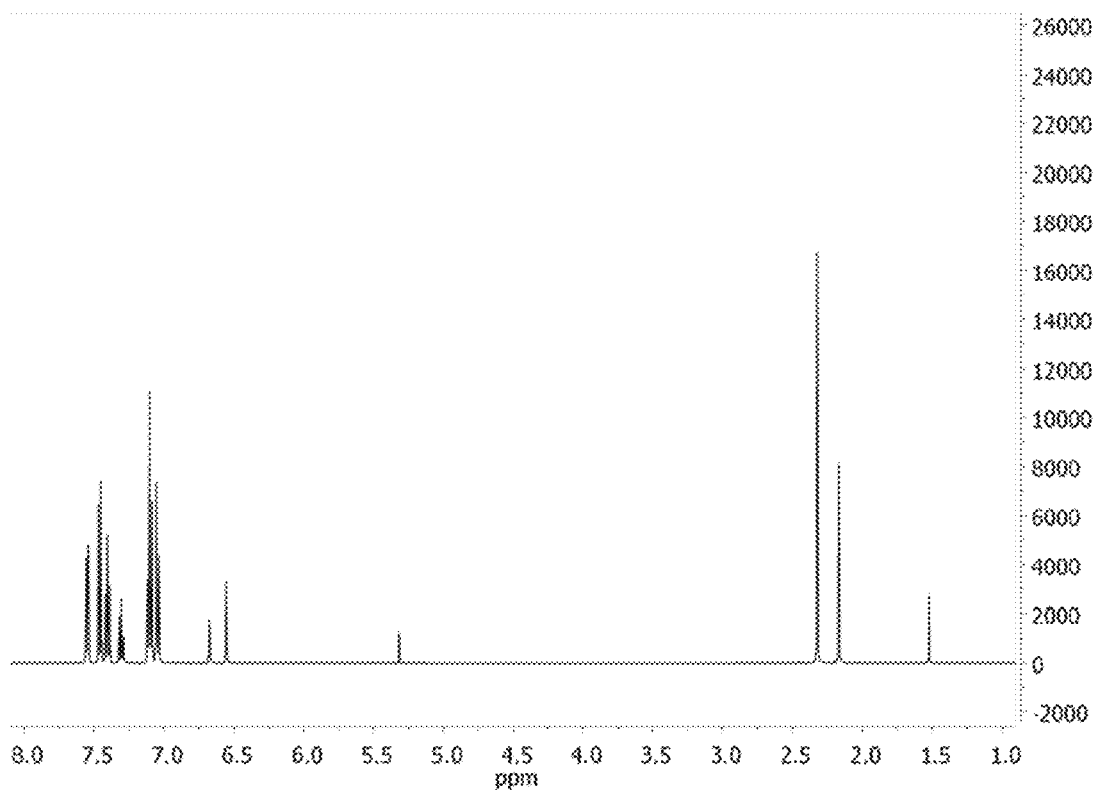

General Procedure for 3,5-dibromophenylenes 1,3,5-Tribromobenzene, the boronic acid and Pd(PPh$_3$)$_4$ were dissolved in a mixture of toluene and ethanol. A degassed 2M aqueous Na$_2$CO$_3$ solution was added. The mixture was refluxed for 18 hours. After cooling to room temperature the organic phase was separated from the aqueous one. The aqueous phase was extracted with toluene three times. The combined organic phases were evaporated to dryness and the residue was filtered over a pad of silica gel using dichloromethane (DCM) as eluent. After evaporating the solvents the crude product was purified by column chromatography on silica gel using hexane:DCM mixtures as an eluent. In thin layer chromatography (TLC), the upper main spot was identified as the desired product and the one below as the 3,5-disubstituted bromobenzene side product.

3,5-dibromo-1,1'-biphenyl

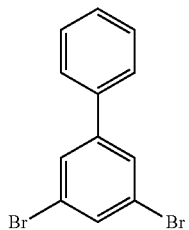 [SMILES: Brc1cc(Br)cc(-c2ccccc2)c1]

1,3,5-tribromobenzene: 10.20 g (1.2 eq, 32.4 mmol)
phenylboronic acid: 3.30 g (1.0 eq, 27.1 mmol)
Pd(PPh$_3$)$_4$: 625 mg (2 mol %, 0.54 mmol)
toluene: 160 mL
ethanol: 54 mL
2M Na$_2$CO$_3$: 27 mL
Yield: 5.53 g (65%)
GC-MS: m/z=310/312/314

3,5-dibromo-3',5'-dimethyl-1,1'-biphenyl

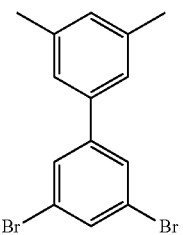

1,3,5-tribromobenzene: 13.00 g (1.2 eq, 41.3 mmol)
3,5-dimethylphenylboronic acid: 5.16 g (1.0 eq, 34.4 mmol)
Pd(PPh$_3$)$_4$: 795 mg (2 mol %, 0.69 mmol)
toluene: 160 mL
ethanol: 68 mL
2M Na$_2$CO$_3$: 34 mL
Yield: 7.13 g (61%)
GC-MS: m/z=338/340/342

3,5-dibromo-1,1':4',1''-terphenyl

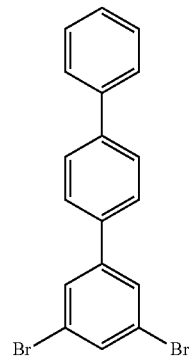 [SMILES: Brc1cc(Br)cc(-c2ccc(-c3ccccc3)cc2)c1]

1,3,5-tribromobenzene: 10.00 g (1.2 eq, 31.77 mmol)
4-biphenylboronic acid: 5.24 g (1.0 eq, 26.47 mmol)
Pd(PPh$_3$)$_4$: 612 mg (2 mol %, 0.53 mmol)
toluene: 160 mL
ethanol: 52 mL
2M Na$_2$CO$_3$: 26 mL
Yield: 4.95 g (48%)
GC-MS: m/z=386/388/390

3,5-dibromo-3'-(trifluoromethyl)-1,1'-biphenyl

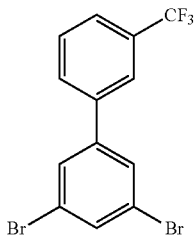 [SMILES: FC(F)(F)c1cccc(-c2cc(Br)cc(Br)c2)c1]

1,3,5-tribromobenzene: 10.00 g (1.2 eq, 31.77 mmol)
3-(Trifluoromethyl)phenylboronic acid: 5.03 g (1.0 eq, 26.47 mmol)
Pd(PPh$_3$)$_4$: 611 mg (2 mol %, 0.53 mmol)
toluene: 160 mL
ethanol: 52 mL
2M Na$_2$CO$_3$: 26 mL
Yield: 5.57 g (56%)
GC-MS: m/z=378/380/382

3-(3,5-dibromophenyl)pyridine

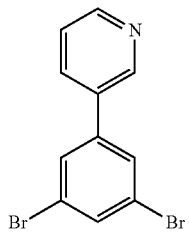 [SMILES: Brc1cc(Br)cc(-c2cccnc2)c1]

1,3,5-tribromobenzene: 10.00 g (1.2 eq, 31.77 mmol)
3-(4,4,5,5-tetramethyl-1,3,2-dioxaborolan-2-yl)pyridine: 5.43 g (1.0 eq, 26.47 mmol)
Pd(PPh$_3$)$_4$: 612 mg (2 mol %, 0.53 mmol)
toluene: 160 mL
ethanol: 52 mL
2M Na$_2$CO$_3$: 26 mL
Yield: 4.00 g (48%)
GC-MS: m/z=311/313/315

General Procedure for Biphenyl Based Cores

The dibromo compound was solved in ether and the flask was shielded from light by aluminium foil. The solution was cooled to −80° C. and butyllithium was added within 30 minutes. After butyllithium addition, the solution was kept at −80° C. for 90 minutes. Under vigorous stirring, copper(II) chloride was added in one shot. The solution was allowed to warm to room temperature and to stir overnight. TLC indicated consumption of the starting material and formation of a new product as the only component in the mixture. The mixture was washed three times with 10% aqueous NH$_4$OH, once with brine and once with water. The organic phase was dried over MgSO$_4$ and filtered through a pad of silica gel by using DCM/hexane 1:1. After evaporation of the solvents, the crude product was washed in boiling methanol for 15 minutes and then filtered and dried.

3,3'-dibromo-1,1'-biphenyl

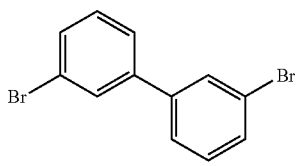 [SMILES: Brc1cccc(-c2cccc(Br)c2)c1]

3,5-dibromobenzene: 58.98 g (1.0 eq, 250 mmol)
n-Butyllithium, 2.5M in hexane: 100 mL (1.0 eq, 250 mmol)
copper(II)chloride: 36.97 g (1.1 eq, 275 mmol)
diethylether: 800 mL
Yield: 22.06 g (56%)
GC-MS: m/z=310/312/314

3,3'-dibromo-5,5'-dimethyl-1,1'-biphenyl

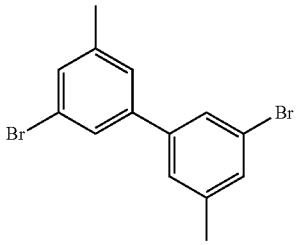 [SMILES: Cc1cc(Br)cc(-c2cc(C)cc(Br)c2)c1]

3,5-dibromotoluene: 62.48 g (1.0 eq, 250 mmol)
n-Butyllithium, 2.5M in hexane: 100 mL (1.0 eq, 250 mmol)
copper(II)chloride: 36.97 g (1.1 eq, 275 mmol)
diethylether: 800 mL
Yield: 22.1 g (52%)
GC-MS: m/z=338/340/342

3,3'-dibromo-5,5'-dimethoxy-1,1'-biphenyl

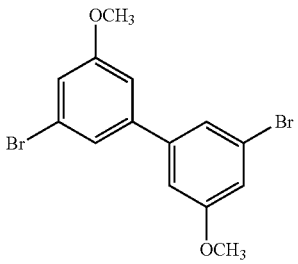 [SMILES: COc1cc(Br)cc(-c2cc(Br)cc(OC)c2)c1]

3,5-dibromoanisole: 16.40 g (1.0 eq, 61.7 mmol)
n-Butyllithium, 2.5M in hexane: 27 mL (1.0 eq, 67.8 mmol)
copper(II)chloride: 9.12 g (1.1 eq, 67.8 mmol)
diethylether: 200 mL
Yield: 9.7 g (85%)
GC-MS: m/z=370/372/374

General Procedure for Secondary Amines

Under an inert atmosphere the bromoaryl component, palladium(II)acetate, cesium carbonate and 2,2'-bis(diphenylphosphino)-1,1'-binaphthyl (BINAP) were combined in a flask and dissolved in 1,4-dioxane. The primary arylamine component was added, followed by heating up the mixture to reflux and stirring for 18-48 hours. According to TLC the reaction was complete. The mixture was cooled to room temperature and filtered through a pad of silica gel. After washing with DCM and evaporation of the solvent the crude product was purified by column chromatography (SiO$_2$, hexane:DCM mixtures). The combined fractions were evaporated to dryness and the resulting solid was recrystalized from hexane to yield the desired product.

N-(p-tolyl)naphthalen-2-amine

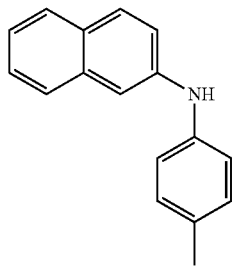 [SMILES: Cc1ccc(Nc2ccc3ccccc3c2)cc1]

2-bromonaphthalene: 15 g (1.0 eq, 72.44 mmol)
p-toluidine: 11.6 g (1.5 eq, 108.6 mmol)
palladium(II)acetate: 488 mg (3.0 mol. %, 2.17 mmol)
BINAP: 2.0 g (4.5 mol. %, 3.26 mmol)
cesium carbonate: 47.20 g (2.0 eq, 144.9 mmol)
dioxane: 150 mL
Yield: 11.4 g (67%)
GC-MS: m/z=233

N-(4-(methyl)phenyl)-[1,1'-biphenyl]-4-amine

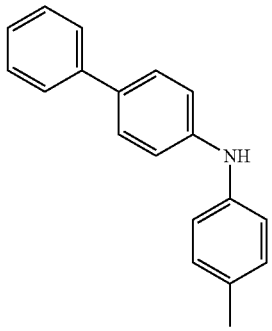 [SMILES: Cc1ccc(Nc2ccc(-c3ccccc3)cc2)cc1]

4-bromobiphenyl: 20.0 g (1.0 eq, 85.8 mmol)
4-toluidine: 9.65 g (1.05 eq, 90.1 mmol)
palladium(II)acetate: 578 mg (3.0 mol. %, 2.6 mmol)
BINAP: 2.40 g (4.5 mol. %, 3.9 mmol)
cesium carbonate: 39.14 g (1.4 eq, 120.1 mmol)
dioxane: 200 mL
Yield: 19.20 g (86%)
EI-MS: m/z=259

N-(4-(tert-butyl)phenyl)-[1,1'-biphenyl]-4-amine

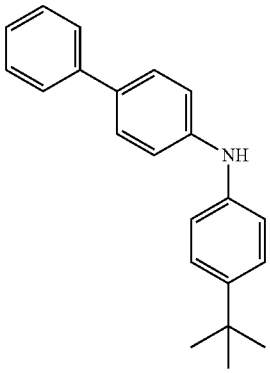 [SMILES: CC(C)(C)c1ccc(Nc2ccc(-c3ccccc3)cc2)cc1]

4-bromobiphenyl: 20 g (1.0 eq, 85.8 mmol)
4-(tert-butyl)aniline: 15.36 g (1.2 eq, 102.9 mmol)
palladium(II)acetate: 578 mg (3.0 mol. %, 2.57 mmol)
BINAP: 2.4 g (4.5 mol. %, 3.86 mmol)
cesium carbonate: 55.90 g (2.0 eq, 171.6 mmol)
dioxane: 220 mL
Yield: 13.9 g (54%)
GC-MS: m/z=301

N-(3,5-dimethylphenyl)-[1,1'-biphenyl]-4-amine

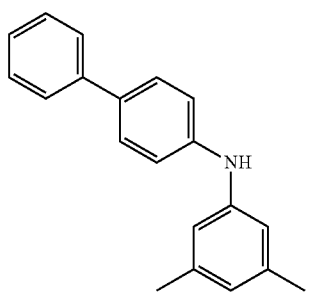 [SMILES: Cc1cc(C)cc(Nc2ccc(-c3ccccc3)cc2)c1]

4-bromobiphenyl: 30.00 g (1.0 eq, 128.70 mmol)
3,5-dimethylaniline: 16.38 g (1.05 eq, 135.10 mmol)
palladium(II)acetate: 867 mg (3.0 mol. %, 3.86 mmol)
BINAP: 3.60 g (4.5 mol. %, 5.79 mmol)
cesium carbonate: 58.70 g (1.4 eq, 180.00 mmol)
dioxane: 300 mL
Yield: 21.34 g (60%)
GC-MS: m/z=273

N-mesityl-[1,1'-biphenyl]-4-amine

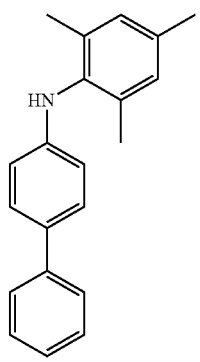 [SMILES: Cc1cc(C)c(Nc2ccc(-c3ccccc3)cc2)c(C)c1]

4-bromobiphenyl: 20.00 g (1.0 eq, 85.8 mmol)
mesitylamine: 12.18 g (1.05 eq, 90.1 mmol)
palladium(II)acetate: 578 mg (3.0 mol. %, 2.57 mmol)
BINAP: 2.40 g (4.5 mol. %, 3.86 mmol)
cesium carbonate: 39.13 g (1.4 eq, 120.1 mmol)
dioxane: 200 mL
Yield: 12.53 g (51%)
GC-MS: m/z=287

General Procedure for Tertiary Amines of the 3,5-diaminophenylene Class

Under an inert atmosphere, the secondary amine, the dibromo compound, bis(dibenzylidenaceton)palladium, tri-tert-butylphosphine and potassium-tert-butoxide were combined in a flask and solved in toluene. The mixture was stirred at 80° C. for 80 minutes and then cooled to room temperature. TLC indicated complete consumption of the starting materials. The mixture was filtered through a pad of silica gel, washed with a 1:2 mixture of DCM/hexane and evaporated to dryness. The crude product was stirred in boiling methanol. After cooling to room temperature, the mixture was filtered to yield the product. In case TLC indicated still some impurities, column chromatography was used. Finally, all tertiary amines were purified by gradient sublimation under high vacuum ($10^{-6}$ mbar) condition.

N1,N3-di([1,1'-biphenyl]-4-yl)-N1,N3-bis(4-(tert-butyl)phenyl)-5-methylbenzene-1,3-diamine (MPD-1)

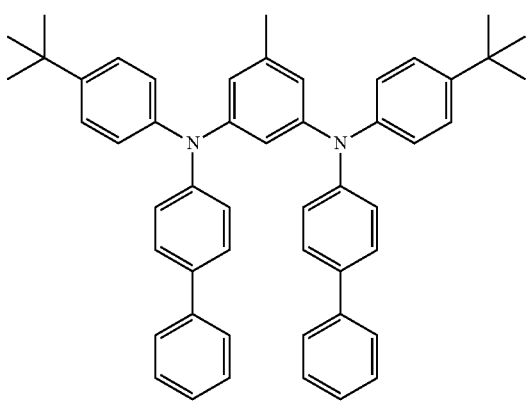 [SMILES: Cc1cc(N(c2ccc(-c3ccccc3)cc2)c2ccc(C(C)(C)C)cc2)cc(N(c2ccc(-c3ccccc3)cc2)c2ccc(C(C)(C)C)cc2)c1]

3,5-dibromotoluene: 2.8 g (1.0 eq, 11.2 mmol)
N-(4-(tert-butyl)phenyl)-[1,1'-biphenyl]-4-amine: 7.1 g (2.1 eq, 23.6 mmol)
bis(dibenzylidenaceton)palladium: 129 mg (2 mol. %, 0.22 mmol)
tri-tert-butylphosphine: 68 mg (3 mol. %, 0.34 mmol)
potassium-tert-butoxide: 3.77 g (3.0 eq, 33.6 mmol)
toluene: 220 mL
Yield: 7.03 g (91%)
HPLC-MS: m/z=691 [M+H$^+$]

5-methyl-N1,N3-di(naphthalen-2-yl)-N1,N3-di-p-tolylbenzene-1,3-diamine (MPD-2) (Comparative Example)

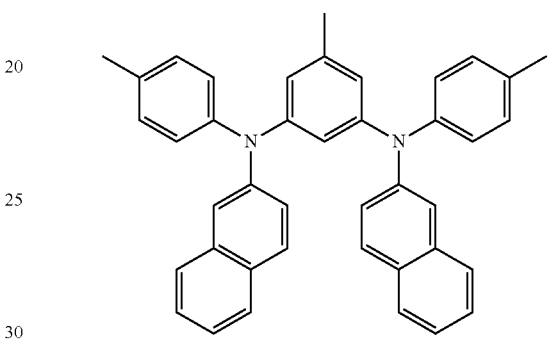

3,5-dibromotoluene: 2.0 g (1.0 eq, 8.0 mmol)
N-(p-tolyl)naphthalen-2-amine: 3.92 g (2.1 eq, 16.8 mmol)
bis(dibenzylidenaceton)palladium: 92 mg (2.0 mol. %, 0.16 mmol)
tri-tert-butylphosphine: 49 mg (3 mol. %, 0.24 mmol)
potassium-tert-butoxide: 2.69 g (3.0 eq, 24 mmol)
toluene: 130 mL
Yield: 3.95 g (70%)
HPLC-MS: m/z=555 [M+H$^+$]

5-methyl-N1,N3-di(naphthalen-1-yl)-N1,N3-diphenylbenzene-1,3-diamine (MPD-3) (Comparative Example)

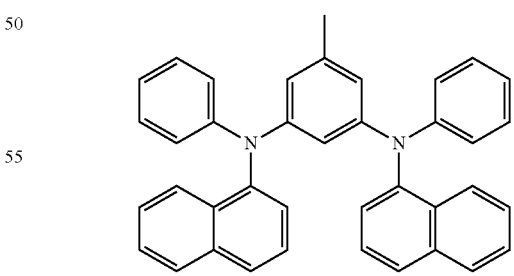

3,5-dibromotoluene: 5.0 g (1.0 eq, 20.0 mmol)
N-phenylnaphthalen-1-amine: 9.21 g (2.1 eq, 42.0 mmol)
bis(dibenzylidenaceton)palladium: 230 mg (2 mol %, 0.40 mmol)
tri-tert-butylphosphine: 121 mg (3 mol. %, 0.60 mmol)
potassium-tert-butoxide: 6.73 g (3.0 eq, 60.0 mmol)

toluene: 150 mL
Yield: 9.31 g (88%)
HPLC-MS: m/z=527 [M+H⁺]

N1,N3-di([1,1'-biphenyl]-4-yl)-N1,N3-bis(4-(tert-butyl)phenyl)-5-methoxybenzene-1,3-d (MPD-4)

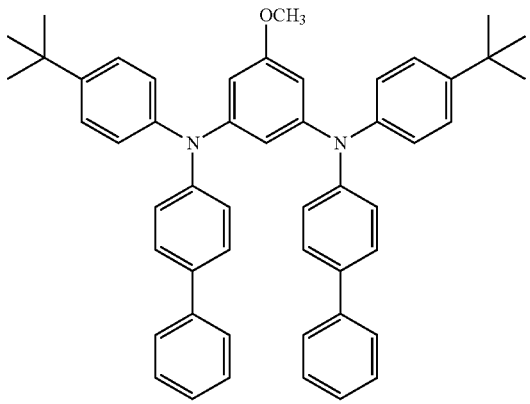 [SMILES: COc1cc(N(c2ccc(-c3ccccc3)cc2)c2ccc(C(C)(C)C)cc2)cc(N(c2ccc(-c3ccccc3)cc2)c2ccc(C(C)(C)C)cc2)c1]

3,5-dibromoanisole: 2.00 g (1.0 eq, 7.50 mmol)
N-(4-(tert-butyl)phenyl)-[1,1'-biphenyl]-4-amine: 4.76 g (2.1 eq, 15.8 mmol)
bis(dibenzylidenaceton)palladium: 86 mg (2.0 mol %, 0.15 mmol)
tri-tert-butylphosphine: 46 mg (3 mol. %, 0.23 mmol)
potassium-tert-butoxide: 2.52 g (3.0 eq, 22.5 mmol)
toluene: 130 mL
Yield: 5.08 g (96%)
HPLC-MS: m/z=707 [M+H⁺]

N3,N5-di([1,1'-biphenyl]-4-yl)-N3,N5-bis(3,5-dimethylphenyl)-[1,1'-biphenyl]-3,5-diamine (MPD-5)

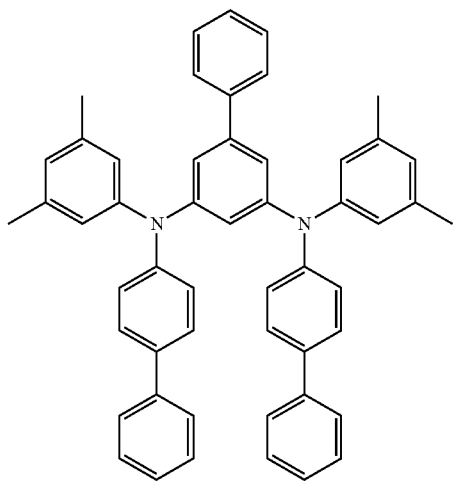

3,5-dibromo-1,1'-biphenyl: 1.9 g (1.0 eq, 6.1 mmol)
N-(3,5-dimethylphenyl)-[1,1'-biphenyl]-4-amine: 3.5 g (2.1 eq, 12.8 mmol)
bis(dibenzylidenaceton)palladium: 70 mg (2 mol. %, 0.12 mmol)
tri-tert-butylphosphine: 37 mg (3 mol. %, 0.18 mmol)
potassium-tert-butoxide: 2.05 g (3.0 eq, 18.3 mmol)
toluene: 150 mL
Yield: 2.94 g (69%)
HPLC-MS: m/z=719 [M+Na⁺]

N3,N5-di([1,1'-biphenyl]-4-yl)-N3,N5-bis(4-(tert-butyl)phenyl)-[1,1'-biphenyl]-3,5-diamine (MPD-6)

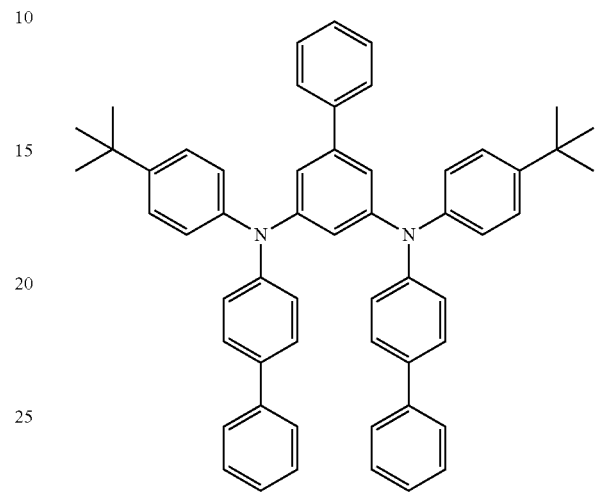

3,5-dibromo-1,1'-biphenyl: 1.80 g (1.0 eq, 5.8 mmol)
N-(4-(tert-butyl)phenyl)-[1,1'-biphenyl]-4-amine: 3.65 g (2.1 eq, 12.1 mmol)
bis(dibenzylidenaceton)palladium: 66 mg (2 mol. %, 0.12 mmol)
tri-tert-butylphosphine: 35 mg (3 mol. %, 0.17 mmol)
potassium-tert-butoxide: 1.94 g (3.0 eq, 17.3 mmol)
toluene: 150 mL
Yield: 4.17 g (96%)
HPLC-MS: m/z=775 [M+Na⁺]

N1,N3-di([1,1'-biphenyl]-4-yl)-N1,N3-bis(3,5-dimethylphenyl)-5-methylbenzene-1,3-diamine (MPD-7)

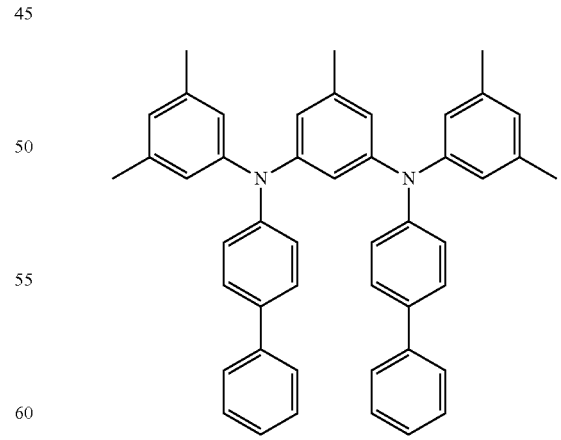

3,5-dibromotoluene: 1.52 g (1.0 eq, 6.1 mmol)
N-(3,5-dimethylphenyl)-[1,1'-biphenyl]-4-amine: 3.50 g (2.1 eq, 12.8 mmol)
bis(dibenzylidenaceton)palladium: 70 mg (2 mol. %, 0.12 mmol)

tri-tert-butylphosphine: 37 mg (3 mol. %, 0.18 mmol)
potassium-tert-butoxide: 2.05 g (3.0 eq, 18.3 mmol)
toluene: 150 mL
Yield: 3.42 g (78%)
HPLC-MS: m/z=657 [M+Na$^+$]

N3,N5-di([1,1'-biphenyl]-4-yl)-N3,N5-bis(3,5-dimethylphenyl)-3',5'-dimethyl-[1,1'-biphenyl]-3,5-diamine (MPD-8)

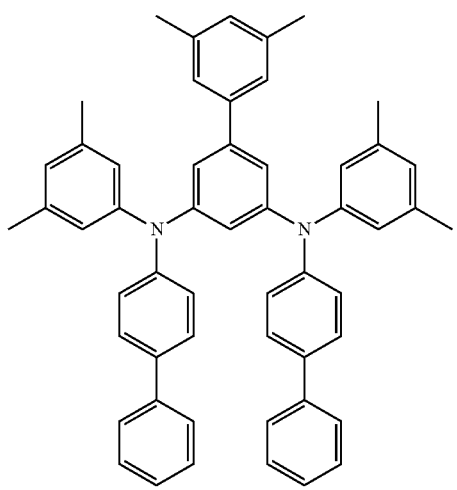

3,5-dibromo-3',5'-dimethyl-1,1'-biphenyl: 2.00 g (1.0 eq, 5.88 mmol)
N N-(3,5-dimethylphenyl)-[1,1'-biphenyl]-4-amine: 3.38 g (2.1 eq, 12.4 mmol)
bis(dibenzylidenaceton)palladium: 68 mg (2 mol. %, 0.12 mmol)
tri-tert-butylphosphine: 36 mg (3 mol. %, 0.18 mmol)
potassium-tert-butoxide: 1.98 g (3.0 eq, 17.6 mmol)
toluene: 120 mL
Yield: 4.02 g (94%)
HPLC-MS: m/z=747 [M+Na$^+$]

N3,N5-di([1,1'-biphenyl]-4-yl)-N3,N5-bis(4-(tert-butyl)phenyl)-3',5'-dimethyl-[1,1'-biphenyl]-3,5-diamine (MPD-9)

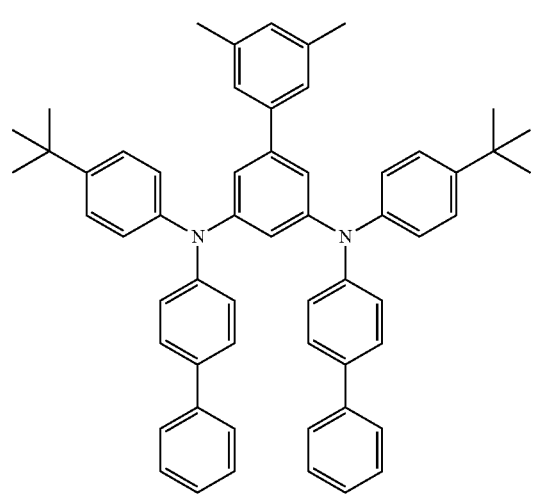 [SMILES: Cc1cc(C)cc(-c2cc(N(c3ccc(-c4ccccc4)cc3)c3ccc(C(C)(C)C)cc3)cc(N(c3ccc(-c4ccccc4)cc3)c3ccc(C(C)(C)C)cc3)c2)c1]

3,5-dibromo-3',5'-dimethyl-1,1'-biphenyl: 2.00 g (1.0 eq, 5.88 mmol)
N-(4-(tert-butyl)phenyl)-[1,1'-biphenyl]-4-amine: 3.72 g (2.1 eq, 12.4 mmol)
bis(dibenzylidenaceton)palladium: 68 mg (2 mol. %, 0.12 mmol)
tri-tert-butylphosphine: 36 mg (3 mol. %, 0.18 mmol)
potassium-tert-butoxide: 1.98 g (3.0 eq, 17.6 mmol)
toluene: 120 mL
Yield: 4.43 g (97%)
HPLC-MS: m/z=803 [M+Na$^+$]

N1,N3-di([1,1'-biphenyl]-4-yl)-N1,N3-bis(4-(tert-butyl)phenyl)-5-(pyridin-3-yl)benzene-1,3-diamine (MPD-10)

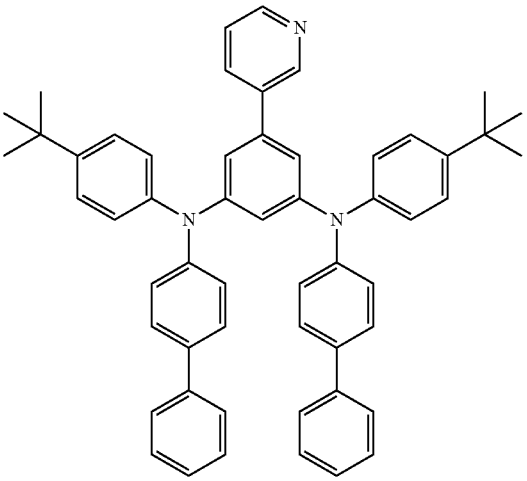 [SMILES: CC(C)(C)c1ccc(N(c2ccc(-c3ccccc3)cc2)c2cc(-c3cccnc3)cc(N(c3ccc(-c4ccccc4)cc3)c3ccc(C(C)(C)C)cc3)c2)cc1]

3-(3,5-dibromophenyl)pyridine: 1.50 g (1.0 eq, 4.8 mmol)
N-(4-(tert-butyl)phenyl)-[1,1'-biphenyl]-4-amine: 3.0 g (2.1 eq, 10.1 mmol)
bis(dibenzylidenaceton)palladium: 55 mg (2 mol. %, 0.10 mmol)
tri-tert-butylphosphine: 29 mg (3 mol. %, 0.14 mmol)
potassium-tert-butoxide: 1.62 g (3.0 eq, 14.4 mmol)
toluene: 120 mL
Yield: 2.40 g (66%)
HPLC-MS: m/z=754 [M+H$^+$]

N3,N5-di([1,1'-biphenyl]-4-yl)-N3,N5-bis(4-(tert-butyl)phenyl)-3'-(trifluoromethyl)-[1,1'-biphenyl]-3,5-diamine (MPD-11)

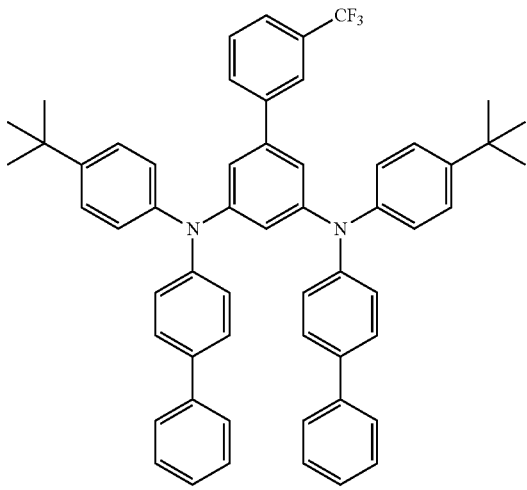 [SMILES: CC(C)(C)c1ccc(N(c2ccc(-c3ccccc3)cc2)c2cc(-c3cccc(C(F)(F)F)c3)cc(N(c3ccc(-c4ccccc4)cc3)c3ccc(C(C)(C)C)cc3)c2)cc1]

3,5-dibromo-3'-(trifluoromethyl)-1,1'-biphenyl: 1.82 g (1.0 eq, 4.8 mmol)
N-(4-(tert-butyl)phenyl)-[1,1'-biphenyl]-4-amine: 3.0 g (2.1 eq, 10.1 mmol)
bis(dibenzylidenaceton)palladium: 55 mg (2 mol. %, 0.10 mmol)
tri-tert-butylphosphine: 29 mg (3 mol. %, 0.14 mmol)
potassium-tert-butoxide: 1.62 g (3.0 eq, 14.4 mmol)
toluene: 120 mL
Yield: 3.29 g (84%)
HPLC-MS: m/z=843 [M+Na$^+$]

N3,N5-di([1,1'-biphenyl]-4-yl)-N3,N5-bis(4-(tert-butyl)phenyl)-[1,1':4',1''-terphenyl]-3,5-diamine (MPD-12)

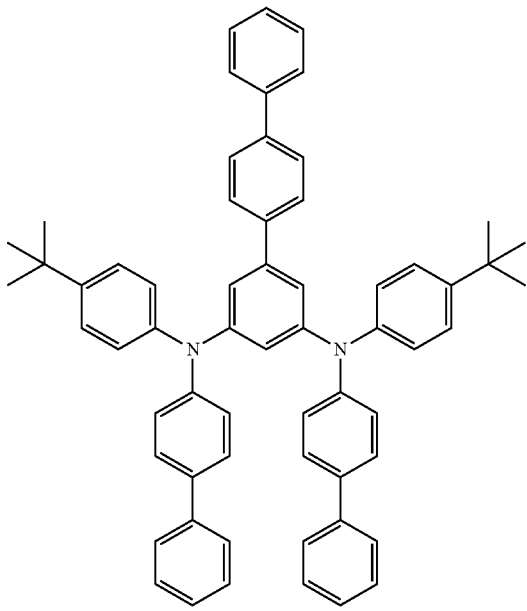 [SMILES: CC(C)(C)c1ccc(N(c2ccc(-c3ccccc3)cc2)c2cc(-c3ccc(-c4ccccc4)cc3)cc(N(c3ccc(-c4ccccc4)cc3)c3ccc(C(C)(C)C)cc3)c2)cc1]

3,5-dibromo-1,1':4',1''-terphenyl: 1.86 g (1.0 eq, 4.8 mmol)
N-(4-(tert-butyl)phenyl)-[1,1'-biphenyl]-4-amine: 3.03 g (2.1 eq, 10.1 mmol)
bis(dibenzylidenaceton)palladium: 55 mg (2 mol. %, 0.10 mmol)
tri-tert-butylphosphine: 29 mg (3 mol. %, 0.14 mmol)
potassium-tert-butoxide: 1.62 g (3.0 eq, 14.4 mmol)
toluene: 120 mL
Yield: 3.20 g (80%)
HPLC-MS: m/z=851 [M+Na$^+$]

N1,N3-di([1,1'-biphenyl]-4-yl)-N1,N3-bis(4-(tert-butyl)phenyl)benzene-1,3-diamine (MPD-13)

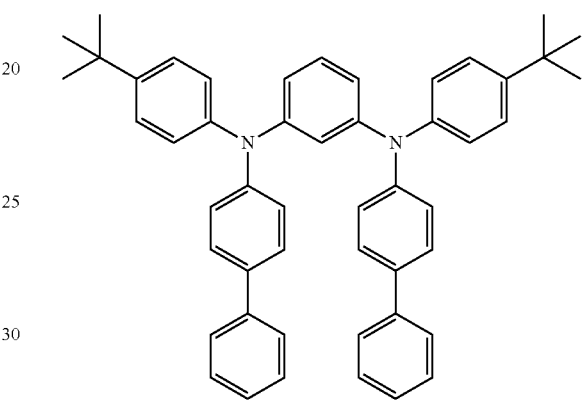

3,5-dibromobenzene: 2.5 g (1.0 eq, 10.6 mmol)
N-(4-(tert-butyl)phenyl)-[1,1'-biphenyl]-4-amine: 6.70 g (2.1 eq, 22.26 mmol)
bis(dibenzylidenaceton)palladium: 121 mg (2 mol. %, 0.21 mmol)
tri-tert-butylphosphine: 64 mg (3 mol. %, 0.32 mmol)
potassium-tert-butoxide: 3.57 g (3.0 eq, 31.8 mmol)
toluene: 180 mL
Yield: 6.70 g (94%)
ESI-MS: m/z=677 [M+H$^+$]

N1,N3-di([1,1'-biphenyl]-4-yl)-N1,N3-bis(3,5-dimethylphenyl)benzene-1,3-diamine (MPD-14)

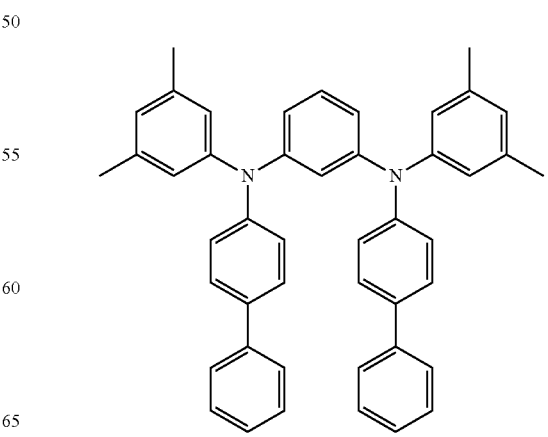

3,5-dibromobenzene: 2.5 g (1.0 eq, 10.6 mmol)
N-(3,5-dimethylphenyl)-[1,1'-biphenyl]-4-amine: 6.08 g (2.1 eq, 22.26 mmol)
bis(dibenzylidenaceton)palladium: 122 mg (2 mol. %, 0.21 mmol)
tri-tert-butylphosphine: 64 mg (3 mol. %, 0.32 mmol)
potassium-tert-butoxide: 3.57 g (3.0 eq, 31.8 mmol)
toluene: 180 mL
Yield: 5.42 g (82%)
ESI-MS: m/z=621 [M+H$^+$]

N1,N3-di([1,1'-biphenyl]-4-yl)-5-methyl-N1,N3-di-p-tolylbenzene-1,3-diamine (MPD-15)

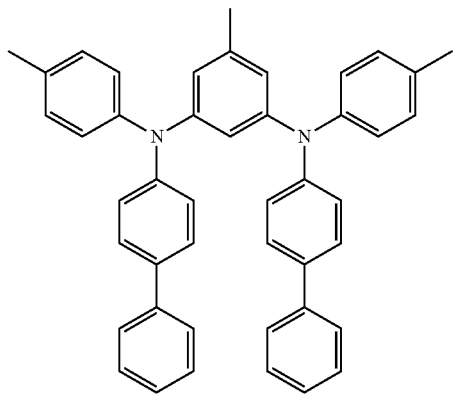

3,5-dibromotoluene: 2.5 g (1.0 eq, 10.0 mmol)
N-(4-(methyl)phenyl)-[1,1'-biphenyl]-4-amine: 5.45 g (2.1 eq, 21.00 mmol)
bis(dibenzylidenaceton)palladium: 115 mg (2 mol. %, 0.20 mmol)
tri-tert-butylphosphine: 61 mg (3 mol. %, 0.30 mmol)
potassium-tert-butoxide: 3.37 g (3.0 eq, 30.0 mmol)
toluene: 180 mL
Yield: 4.95 g (81%).
ESI-MS: m/z=607 [M+H$^+$]

N1,N3-di([1,1'-biphenyl]-4-yl)-N1,N3-dimesityl-5-methylbenzene-1,3-diamine (MPD-16)

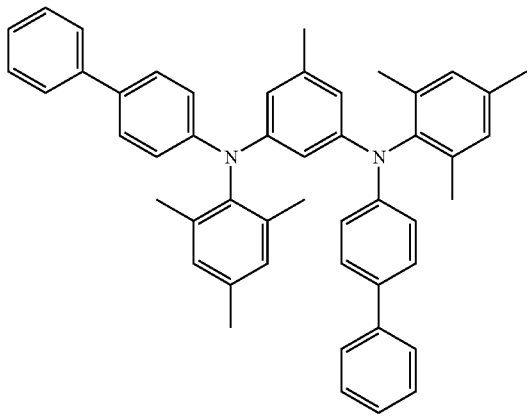 [SMILES: Cc1cc(N(c2ccc(-c3ccccc3)cc2)c2c(C)cc(C)cc2C)cc(N(c2ccc(-c3ccccc3)cc2)c2c(C)cc(C)cc2C)c1]

3,5-dibromotoluene: 16.60 g (1.0 eq, 66.4 mmol)
N-mesityl-[1,1'-biphenyl]-4-amine: 40.1 g (2.1 eq, 139.5 mmol)
bis(dibenzylidenaceton)palladium: 764 mg (2 mol. %, 1.3 mmol)
tri-tert-butylphosphine: 404 mg (3 mol. %, 2.00 mmol)
potassium-tert-butoxide: 22.36 g (3.0 eq, 199.3 mmol)
toluene: 400 mL
Yield: 22.3 g (51%)
HPLC-MS: m/z=663 [M+H$^+$]

General Procedure for Tertiary Amines of the 3,3-diaminobiphenylene Class

The dibromo compound, the secondary amine, bis(dibenzylidenaceton)palladium, tri-tert-butylphosphine and potassium-tert-butoxide were combined in a flask and solved in toluene. The mixture was stirred at 80° C. until TLC indicated complete consumption of the starting materials. The mixture was filtered through a pad of silica gel, washed with DCM and evaporated to dryness. The crude solid was washed in boiling methanol and filtered afterwards. This sequence was repeated with hot hexane and hot acetone to yield the desired product finally.

N3,N3'-di([1,1'-biphenyl]-4-yl)-N3,N3'-bis(4-(tert-butyl)phenyl)-5,5'-dimethyl-[1,1'-biphenyl]-3,3'-diamine (MDAB-1)

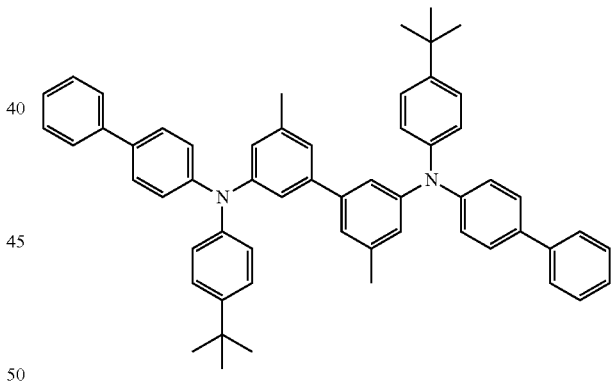

3,3'-dibromo-5,5'-dimethyl-1,1'-biphenyl: 2.00 g (1.0 eq, 5.88 mmol)
N-(4-(tert-butyl)phenyl)-[1,1'-biphenyl]-4-amine: 3.90 g (2.1 eq, 12.9 mmol)
bis(dibenzylidenaceton)palladium: 68 mg (2.0 mol. %, 0.12 mmol)
tri-tert-butylphosphine: 36 mg (3.0 mol. %, 0.18 mmol)
potassium-tert-butoxide: 1.98 g (3.0 eq, 17.6 mmol)
toluene: 150 mL
Yield: 2.27 g (49%)
HPLC-MS: m/z=781 [M+H$^+$]

29

N3,N3'-di([1,1'-biphenyl]-4-yl)-N3,N3'-bis(4-(tert-butyl)phenyl)-5,5'-dimethoxy-[1,1'-biphenyl]-3,3'-diamine (MDAB-2)

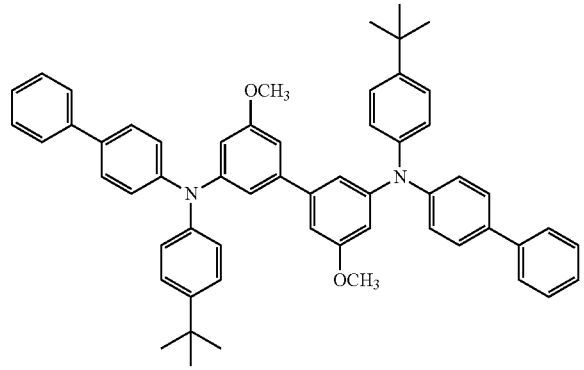 [SMILES: COc1cc(-c2cc(OC)cc(N(c3ccc(-c4ccccc4)cc3)c3ccc(C(C)(C)C)cc3)c2)cc(N(c2ccc(-c3ccccc3)cc2)c2ccc(C(C)(C)C)cc2)c1]

3,3'-dibromo-5,5'-dimethoxy-1,1'-biphenyl: 2.00 g (1.0 eq, 5.88 mmol)
N-(4-(tert-butyl)phenyl)-[1,1'-biphenyl]-4-amine: 3.56 g (2.2 eq, 11.8 mmol)
bis(dibenzylidenaceton)palladium: 62 mg (2.0 mol. %, 0.11 mmol)
tri-tert-butylphosphine: 33 mg (3.0 mol. %, 0.16 mmol)
potassium-tert-butoxide: 1.81 g (3.0 eq, 16.1 mmol)
toluene: 130 mL
Yield: 3.33 g (76%)
HPLC-MS: m/z=835 [M+Na$^+$]

N3,N3'-di([1,1'-biphenyl]-4-yl)-N3,N3'-bis(3,5-dimethylphenyl)-5,5'-dimethyl-[1,1'-biphenyl]-3,3'-diamine (MDAB-3)

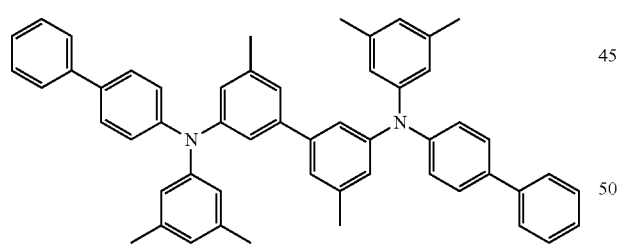

3,3'-dibromo-5,5'-dimethyl-1,1'-biphenyl: 5.43 g (1.0 eq, 15.96 mmol)
N-(3,5-dimethylphenyl)-[1,1'-biphenyl]-4-amine: 9.61 g (2.1 eq, 33.51 mmol)
bis(dibenzylidenaceton)palladium: 184 mg (2.0 mol. %, 0.32 mmol)
tri-tert-butylphosphine: 202 mg (3.0 mol. %, 0.48 mmol)
potassium-tert-butoxide: 5.37 g (3.0 eq, 47.88 mmol)
toluene: 250 mL
Yield: 10.56 g (91%)
HPLC-MS: m/z=747 [M+Na$^+$]

30

N3,N3'-di([1,1'-biphenyl]-4-yl)-N3,N3'-diphenyl-[1,1'-biphenyl]-3,3'-diamine (MDAB-4)

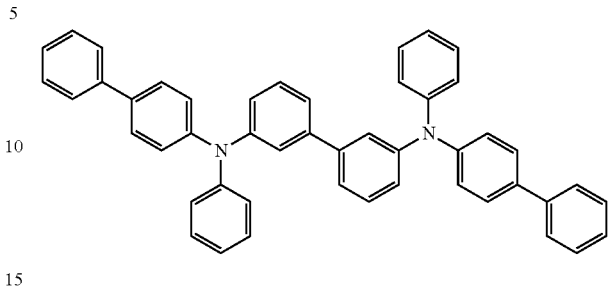

3,3'-dibromo-1,1'-biphenyl: 3.39 g (1.0 eq, 10.88 mmol)
N-(3,5-dimethylphenyl)-[1,1'-biphenyl]-4-amine: 5.60 g (2.1 eq, 22.84 mmol)
bis(dibenzylidenaceton)palladium: 125 mg (2.0 mol. %, 0.22 mmol)
tri-tert-butylphosphine: 66 mg (3.0 mol. %, 0.33 mmol)
potassium-tert-butoxide: 3.66 g (3.0 eq, 32.6 mmol)
toluene: 190 mL
Yield: 6.8 g (97%)
EI-MS: m/z=640

5,5'-dimethyl-N3,N3,N3',N3'-tetra-m-tolyl-[1,1'-biphenyl]-3,3'-diamine (MDAB-5)

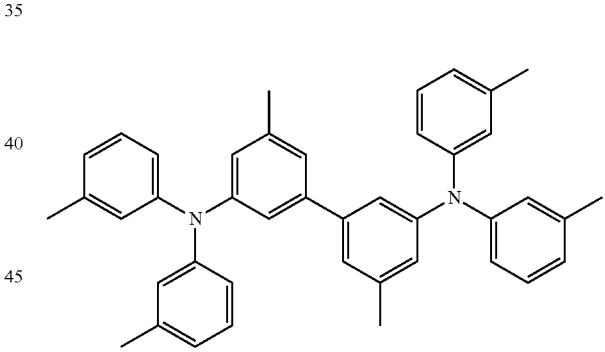

3,3'-dibromo-5,5'-dimethyl-1,1'-biphenyl: 2.50 g (1.0 eq, 7.35 mmol)
-3,3'-dimethyldiphenylamine: 3.05 g (2.1 eq, 15.44 mmol)
bis(dibenzylidenaceton)palladium: 85 mg (2.0 mol. %, 0.15 mmol)
tri-tert-butylphosphine: 45 mg (3.0 mol. %, 0.22 mmol)
potassium-tert-butoxide: 2.50 g (3.0 eq, 22.05 mmol)
toluene: 180 mL
Yield: 2.8 g (66%)
EI-MS: m/z=572

N3,N3'-di([1,1'-biphenyl]-4-yl)-N3,N3'-dimesityl-5,5'-dimethyl-[1,1'-biphenyl]-3,3'-diamine

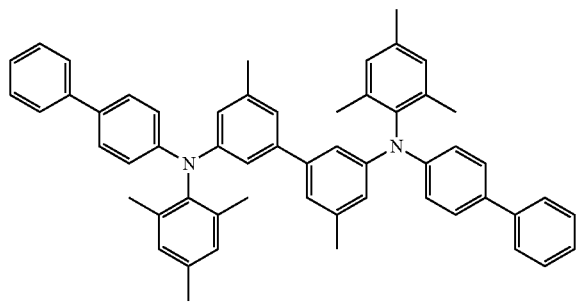 [SMILES: Cc1cc(-c2cc(C)cc(N(c3ccc(-c4ccccc4)cc3)c3c(C)cc(C)cc3C)c2)cc(N(c2ccc(-c3ccccc3)cc2)c2c(C)cc(C)cc2C)c1]

3,5-dibromo-3',5'-dimethyl-1,1'-biphenyl: 20.00 g (1.0 eq, 58.8 mmol)
N-mesityl-[1,1'-biphenyl]-4-amine: 35.50 g (2.1 eq, 123.5 mmol)
bis(dibenzylidenaceton)palladium: 676 mg (2 mol. %, 1.20 mmol)
tri-tert-butylphosphine: 364 mg (3 mol. %, 1.80 mmol)
potassium-tert-butoxide: 19.80 g (3.0 eq, 176.4 mmol)
toluene: 700 mL
Yield: 27.1 g (61%)
HPLC-MS: m/z=753 [M+H$^+$]

N3,N3'-di([1,1'-biphenyl]-4-yl)-N3,N3'-dimesityl-[1,1'-biphenyl]-3,3'-diamine (MDAB-7)

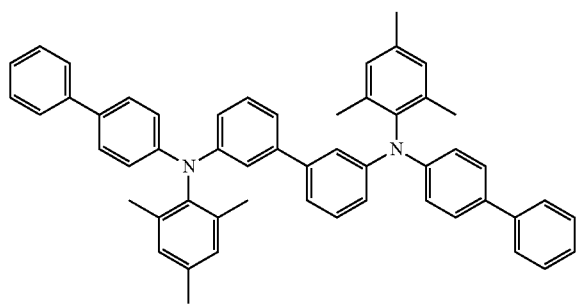 [SMILES: Cc1cc(C)c(N(c2ccc(-c3ccccc3)cc2)c2cccc(-c3cccc(N(c4ccc(-c5ccccc5)cc4)c4c(C)cc(C)cc4C)c3)c2)c(C)c1]

3,5-dibromo-1,1'-biphenyl: 5.17 g (1.0 eq, 16.59 mmol)
N-mesityl-[1,1'-biphenyl]-4-amine: 10.00 g (2.1 eq, 34.79 mmol)
bis(dibenzylidenaceton)palladium: 190 mg (2 mol. %, 0.33 mmol)
tri-tert-butylphosphine: 100 mg (3 mol. %, 0.50 mmol)
potassium-tert-butoxide: 5.58 g (3.0 eq, 49.77 mmol)
toluene: 230 mL
Yield: 8.7 g (72%)
EI-MS: m/z=724

OLED Preparation and Testing

Performance testing of the new materials was carried out in bottom emitting phosphorescent organic light emitting diodes (OLED). The diodes were processed in vacuum via vapor thermal deposition of organic materials (active layers) and metals (electrodes). Shadow mask techniques were used to structure the devices (active matrix, electrodes). Four OLEDs are prepared on one substrate with an active area of 6.70 mm$^2$ each. 16 identical indium tin oxide (ITO) substrates were processed at once in a 4×4 array placed on a table which is pivotable around its vertical axe. Using shutters, each of these 16 substrates can be covered by different set of organic layers. The ITO substrates were cleaned and put into a vapor thermal deposition unit in the 4×4 array. A reference p-doped layer (e.g. H-1 doped with D1; molar ratio (97:3) was deposited on half of these substrates for a final film thickness of 30 nm. On the other half of the plate, the studied inventive material was codeposited with the same p-dopant at the same 97:3 molar ratio and thickness. After a rotation of the plate by 90°, the second (electron blocking) layer is deposited on top of the first layer. Here, half the plate is covered with 10 nm of the reference compound (e.g., TCTA) and the other half with the same inventive material as used in the first layer (see FIG. 1). The reference devices (FIG. 1, field D) were thus always processed together with the devices comprising the inventive materials. This approach allows assessing performance of new material in comparison with the reference independent from possible day-to-day variations of deposition rates, vacuum quality or other tool performance parameters. As each field contains 16 identically prepared OLEDs and the performance parameters were estimated for each of these 16 OLEDs, statistical evaluation of the obtained experimental results unequivocally showed the statistical significance of the observed average values reported in the Table 1.

The subsequent phosphorescent green emission layer (Merck_TMM004:Irrpy at molar ratio 9:1) was deposited with a thickness of 20 nm, followed by 10 nm Merck_TMM004 as a hole blocking layer and 50 nm E-1 layer doped with D2 (matrix to dopant molar ratio 9:1). The cathode was prepared by vacuum deposition of 100 nm aluminum layer.

Bottom emitting blue fluorescent OLEDs were prepared on ITO substrates and tested analogously, with a difference that Sun Fine Chem (SFC, Korea) host ABH113 and blue emitter NUBD370 were codeposited in the weight ratio 97:3 as a 20 nm thick emitting layer, followed by 36 nm thick electron transporting layer consisting of 60 weigt % E2 and 40 weight % lithium 8-hygroxyquinoline salt (LiQ). The 100 nm aluminium cathode was deposited on top of the electron transporting layer.

In comparison with devices comprising H-2 in the same hole transporting and/or electron blocking layer, the devices comprising inventive compounds showed improvement in terms of the overall performance score Q as defined in the Table 1 in the range 3-22%.

The features disclosed in the foregoing description and in the claims may, both separately and in any combination, be material for realizing the invention in diverse forms thereof.

The invention claimed is:

1. A compound represented by general formula (I)

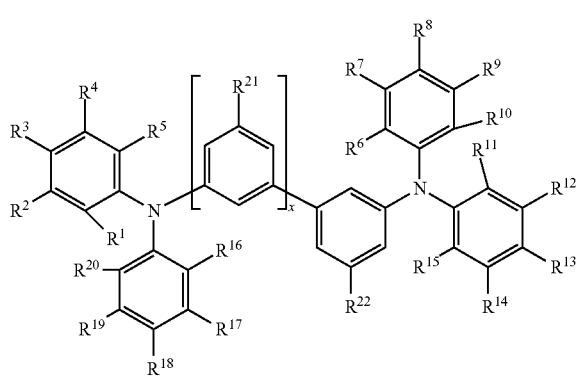

I wherein $R^1$-$R^{20}$ are independently selected from hydrogen, C1-C20 alkyl, C3-C20 cycloalkyl, C1-C20 alkoxy, C3-C20 cycloalkyloxy, C7-C20 arylalkyl, C6-C20 aryl, or C2-C20 heteroaryl;
i) at least one of $R^1$-$R^5$ and at least one of $R^{11}$-$R^{15}$ is C6-C20 aryl or C2-C20 heteroaryl,
ii) $R^1$ with $R^2$ as well as $R^{11}$ with $R^{12}$ form an aromatic ring, or
iii) $R^2$ with $R^3$ as well as $R^{12}$ with $R^{13}$ form an aromatic ring;
at least two of $R^6$-$R^{10}$ and at least two of $R^{16}$-$R^{20}$ are methyl, or at least one of $R^6$-$R^{10}$ and at least one of $R^{16}$-$R^{20}$ is selected from C2-C20 alkyl, C3-C20 cycloalkyl, C1-C20 alkoxy, C3-C20 cycloalkyloxy, C7-C20 arylalkyl, C6-C20 aryl, or C2-C20 heteroaryl, and
x is an integer selected from 0 or 1, wherein when x is 0, $R^{22}$ is selected from C3-C20 cycloalkyl, C3-C20 cycloalkyloxy, C7-C20 arylalkyl, C2-C20 heteroaryl, wherein when x is 1, $R^{21}$ and $R^{22}$ are independently selected from C1-C10 alkyl, C3-C10 cycloalkyl, C1-C10 alkoxy, or C3-C10 cycloalkyloxy.

2. The compound according to claim 1, wherein
i) at least one of $R^1$-$R^5$ and at least one of $R^{11}$-$R^{15}$ is C6-C20 aryl or C2-C20 heteroaryl,
ii) $R^1$ with $R^2$ as well as $R^{11}$ with $R^{12}$ form an aromatic ring, or
iii) $R^2$ with $R^3$ as well as $R^{12}$ with $R^{13}$ form an aromatic ring;
at least two of $R^6$-$R^{10}$ and at least two of $R^6$-$R^{20}$ are methyl, or at least one of $R^6$-$R^{10}$ and at least one of $R^{16}$-$R^{20}$ is selected from C2-C20 alkyl, C3-C20 cycloalkyl, C1-C20 alkoxy, C3-C20 cycloalkyloxy, C7-C20 arylalkyl, C6-C20 aryl, or C2-C20 heteroaryl, whereas other $R^6$-$R^{10}$ and $R^{16}$-$R^{20}$ are H.

3. The compound according to claim 2, wherein
at least one of $R^1$-$R^5$ and at least one of $R^{11}$-$R^{15}$ is C6-C20 aryl or C2-C20 heteroaryl;
at least two of $R^6$-$R^{10}$ and at least two of $R^{16}$-$R^{20}$ are methyl, or
at least one of $R^6$-$R^{10}$ and at least one of $R^{16}$-$R^{20}$ is selected from C2-C20 alkyl, C3-C20 cycloalkyl, C1-C20 alkoxy, C3-C20 cycloalkyloxy, C7-C20 arylalkyl, C6-C20 aryl, or C2-C20 heteroaryl,
wherein other $R^1$-$R^5$, $R^6$-$R^{10}$, $R^{11}$-$R^{15}$ and $R^{16}$-$R^{20}$ are H.

4. The compound according to claim 3, wherein
at least one of $R^1$-$R^5$ and at least one of $R^{11}$-$R^{15}$ is phenyl;
at least two of $R^6$-$R^{10}$ and at least two of $R^{16}$-$R^{20}$ are methyl, or
at least one of $R^6$-$R^{10}$ and at least one of $R^{16}$-$R^{20}$ is selected from C2-C20 alkyl, C3-C20 cycloalkyl, C1-C20 alkoxy, C3-C20 cycloalkyloxy, C7-C20 arylalkyl, C6-C20 aryl, or C2-C20 heteroaryl,
wherein other $R^1$-$R^5$, $R^6$-$R^{10}$, $R^{11}$-$R^{15}$ and $R^{16}$-$R^{20}$ are H.

5. The compound according to claim 1, wherein the compound is represented by formula (III)

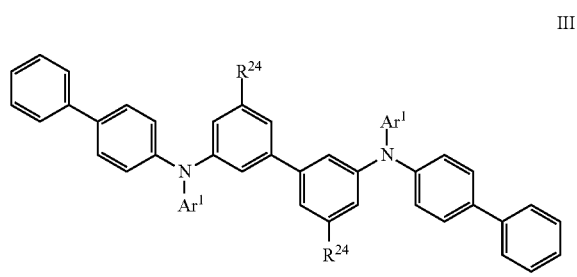

III wherein $Ar^1$ is selected from 4-tert-butylphenyl, 3,5-dimethylphenyl, or 2,4,6-trimethylphenyl, and $R^{24}$ is selected from C1-C10 alkyl, C3-C10 cycloalkyl, C1-C10 alkoxy or C3-C10 cycloalkyloxy.

6. A compound represented by general formula (I)

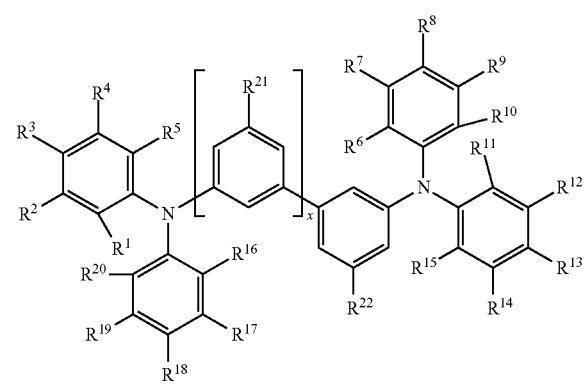

I wherein $R^1$-$R^{20}$ are independently selected from hydrogen, C3-C20 cycloalkyl, C3-C20 cycloalkyloxy, C7-C20 arylalkyl, C6-C20 aryl, or C2-C20 heteroaryl;
i) at least one of $R^1$-$R^5$ and at least one of $R^{11}$-$R^{15}$ is C6-C20 aryl or C2-C20 heteroaryl,
ii) $R^1$ with $R^2$ as well as $R^{11}$ with $R^{12}$ form an aromatic ring, or
iii) $R^2$ with $R^3$ as well as $R^{12}$ with $R^{13}$ form an aromatic ring;
at least one of $R^6$-$R^{10}$ and at least one of $R^{16}$-$R^{20}$ is selected from C3-C20 cycloalkyl, C3-C20 cycloalkyloxy, C7-C20 arylalkyl, C6-C20 aryl, or C2-C20 heteroaryl,
and
x is an integer selected from 0 or 1, wherein when x is 0, $R^{22}$ is selected from C3-C20 cycloalkyl, C3-C20 cycloalkyloxy, C7-C20 arylalkyl, C6-C20 aryl, or C2-C20 heteroaryl, wherein when x is 1, $R^{21}$ and $R^{22}$ are independently selected from C1-C10 alkyl, C3-C10 cycloalkyl, C1-C10 alkoxy, or C3-C10 cycloalkyloxy.

7. A compound represented by general formula (I)

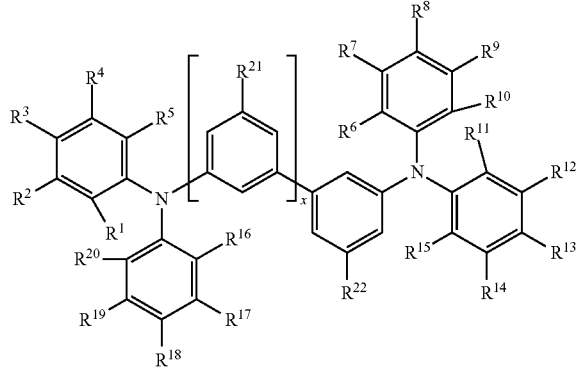

I wherein $R^1$-$R^{20}$ are independently selected from hydrogen, C1-C20 alkyl, C3-C20 cycloalkyl, C1-C20 alkoxy, C3-C20 cycloalkyloxy, C7-C20 arylalkyl, C6-C20 aryl, or C2-C20 heteroaryl;
i) at least one of $R^1$-$R^5$ and at least one of $R^{11}$-$R^{15}$ is C6-C20 aryl or C2-C20 heteroaryl,
ii) $R^1$ with $R^2$ as well as with $R^{12}$ form an aromatic ring, or
iii) $R^2$ with $R^3$ as well as $R^{12}$ with $R^{13}$ form an aromatic ring;
at least two of $R^6$-$R^{10}$ and at least two of $R^{16}$-$R^{20}$ are methyl, or at least one of $R^6$-$R^{10}$ and at least one of $R^{16}$-$R^{20}$ is selected from C2-C20 alkyl, C3-C20 cycloalkyl, C1-C20 alkoxy, C3-C20 cycloalkyloxy, C7-C20 arylalkyl, C6-C20 aryl, or C2-C20 heteroaryl, and
x is 1, wherein $R^{21}$ and $R^{22}$ are independently selected from C1-C10 alkyl, C3-C10 cycloalkyl, C1-C10 alkoxy, or C3-C10 cycloalkyloxy.

8. A compound represented by formula (II)

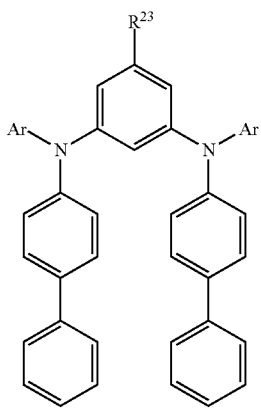

II wherein $R^{23}$ is hydrogen, C1-C20 alkyl, C3-C20 cycloalkyl, C1-C10 alkoxy, C3-C20 cycloalkyloxy, C7-C20 arylalkyl, C6-C20 aryl, or C2-C20 heteroaryl, and Ar is selected from 4-tert-butylphenyl, 3,5-dimethylphenyl, or 2,4,6-trimethylphenyl.

9. The compound according to claim 8, represented by formula (IV):

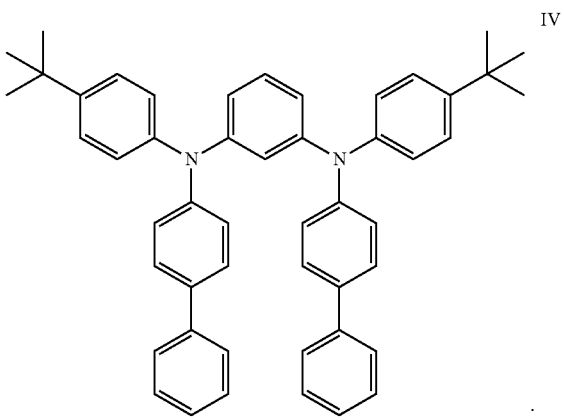 [SMILES: CC(C)(C)c1ccc(N(c2ccc(-c3ccccc3)cc2)c2cccc(N(c3ccc(-c4ccccc4)cc3)c3ccc(C(C)(C)C)cc3)c2)cc1]

IV

10. The compound according to claim 8, represented by formula (V):

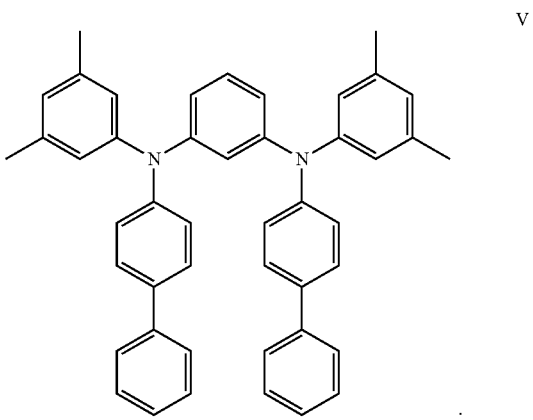

V

* * * * *